(12) United States Patent
Bryson et al.

(10) Patent No.: US 10,285,953 B2
(45) Date of Patent: *May 14, 2019

(54) SUBLINGUAL FILMS

(71) Applicant: Sunovion Pharmaceuticals Inc., Marlborough, MA (US)

(72) Inventors: Nathan John Bryson, Toronto (CA); Anthony John Giovinazzo, Caledon (CA); Scott David Barnhart, York, PA (US); Michael Clinton Koons, York, PA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,992

(22) Filed: Aug. 2, 2016

(65) Prior Publication Data
US 2016/0338972 A1 Nov. 24, 2016

Related U.S. Application Data

(63) Continuation of application No. 15/014,655, filed on Feb. 3, 2016, now Pat. No. 9,427,412, which is a
(Continued)

(51) Int. Cl.
| | |
|---|---|
| A61K 9/70 | (2006.01) |
| A61F 13/00 | (2006.01) |
| A61K 31/435 | (2006.01) |
| A61K 31/473 | (2006.01) |
| A61K 31/485 | (2006.01) |
| A61K 31/4415 | (2006.01) |
| A61K 47/02 | (2006.01) |
| A61K 9/00 | (2006.01) |
| A61K 47/14 | (2017.01) |
| A61K 47/38 | (2006.01) |
| A61K 31/4045 | (2006.01) |
| A61K 45/06 | (2006.01) |
| A61K 31/381 | (2006.01) |
| A61K 31/428 | (2006.01) |
| A61K 31/48 | (2006.01) |
| A61K 31/4985 | (2006.01) |
| A61K 31/506 | (2006.01) |
| A61J 1/03 | (2006.01) |
| A61J 7/00 | (2006.01) |
| B29C 39/18 | (2006.01) |
| B65D 65/38 | (2006.01) |
| A61K 47/10 | (2017.01) |
| A61K 47/12 | (2006.01) |
| A61K 47/18 | (2017.01) |
| A61K 47/22 | (2006.01) |
| A61K 47/36 | (2006.01) |
| B29C 39/38 | (2006.01) |
| B29C 43/30 | (2006.01) |

(Continued)

(52) U.S. Cl.
CPC ...... *A61K 9/7007* (2013.01); *A61F 13/00063* (2013.01); *A61J 1/03* (2013.01); *A61J 7/0053* (2013.01); *A61K 9/006* (2013.01); *A61K 31/381* (2013.01); *A61K 31/4045* (2013.01); *A61K 31/428* (2013.01); *A61K 31/4415* (2013.01); *A61K 31/473* (2013.01); *A61K 31/48* (2013.01); *A61K 31/485* (2013.01); *A61K 31/4985* (2013.01); *A61K 31/506* (2013.01); *A61K 45/06* (2013.01); *A61K 47/02* (2013.01); *A61K 47/10* (2013.01); *A61K 47/12* (2013.01); *A61K 47/14* (2013.01); *A61K 47/183* (2013.01); *A61K 47/22* (2013.01); *A61K 47/36* (2013.01); *A61K 47/38* (2013.01); *B29C 39/18* (2013.01); *B29C 39/38* (2013.01); *B29C 43/305* (2013.01); *B29C 43/52* (2013.01); *B29C 65/70* (2013.01); *B29C 66/45* (2013.01); *B65D 65/38* (2013.01); *A61K 9/209* (2013.01); *B29K 2001/00* (2013.01); *B29L 2007/008* (2013.01); *B29L 2009/00* (2013.01); *B29L 2031/753* (2013.01); *B29L 2031/755* (2013.01)

(58) Field of Classification Search
CPC ........ A61K 9/0056–9/006; A61K 9/70; A61K 9/7007; A61K 31/435; A61K 31/473; A61K 31/485
See application file for complete search history.

(56) References Cited

U.S. PATENT DOCUMENTS

| | | |
|---|---|---|
| 1,234,123 A | 7/1917 | Bond |
| 3,972,995 A | 8/1976 | Tsuk et al. |

(Continued)

FOREIGN PATENT DOCUMENTS

| | | |
|---|---|---|
| AU | 746373 B2 | 4/2002 |
| CA | 02274893 A1 | 6/1998 |

(Continued)

OTHER PUBLICATIONS

"R-(-)-Apomorphine hydrochloride hemihydrate, calcined," <http://www.sigmaaldrich.com/content/dam/sigma-aldrich/docs/Sigma/Product_Information_Sheet/a4393pis.pdf>, accessed on Oct. 26, 2015 (1 page).

(Continued)

*Primary Examiner* — H. Sarah Park
(74) *Attorney, Agent, or Firm* — Clark & Elbing LLP

(57) ABSTRACT

The invention features sublingual film formulations of dopamine agonists and methods of treating Parkinson's disease, tremors, restless leg syndrome, sexual dysfunction, and depressive disorders therewith.

22 Claims, 4 Drawing Sheets

Related U.S. Application Data continuation of application No. 14/478,975, filed on Sep. 5, 2014, now Pat. No. 9,283,219, which is a continuation of application No. 13/858,638, filed on Apr. 8, 2013, now Pat. No. 8,846,074, which is a continuation of application No. 13/445,656, filed on Apr. 12, 2012, now Pat. No. 8,414,922, which is a continuation of application No. PCT/US2011/065665, filed on Dec. 16, 2011.

(60) Provisional application No. 61/483,864, filed on May 9, 2011, provisional application No. 61/423,858, filed on Dec. 16, 2010.

(51) Int. Cl.
| | |
|---|---|
| *B29C 43/52* | (2006.01) |
| *B29C 65/70* | (2006.01) |
| *B29C 65/00* | (2006.01) |
| *A61K 9/24* | (2006.01) |
| *B29K 1/00* | (2006.01) |
| *B29L 31/00* | (2006.01) |
| *B29L 7/00* | (2006.01) |
| *B29L 9/00* | (2006.01) |

(56) References Cited

U.S. PATENT DOCUMENTS

| | | | |
|---|---|---|---|
| 4,614,545 | A | 9/1986 | Hess |
| 5,047,244 | A | 9/1991 | Sanvordeker et al. |
| 5,441,747 | A | 8/1995 | de Haan et al. |
| 5,523,090 | A | 6/1996 | Znaiden et al. |
| 5,560,932 | A | 10/1996 | Bagchi et al. |
| 5,624,677 | A | 4/1997 | El-Rashidy et al. |
| 5,629,003 | A | 5/1997 | Horstmann et al. |
| 5,700,478 | A | 12/1997 | Biegajski et al. |
| 5,888,534 | A | 3/1999 | El-Rashidy et al. |
| 5,945,117 | A | 8/1999 | El-Rashidy et al. |
| 5,994,363 | A | 11/1999 | El-Rashidy et al. |
| 6,087,362 | A | 7/2000 | El-Rashidy |
| 6,121,276 | A | 9/2000 | El-Rashidy et al. |
| 6,159,498 | A | 12/2000 | Tapolsky et al. |
| 6,177,096 | B1 | 1/2001 | Zerbe et al. |
| 6,193,992 | B1 | 2/2001 | El-Rashidy et al. |
| 6,200,983 | B1 | 3/2001 | El-Rashidy et al. |
| 6,264,981 | B1 | 7/2001 | Zhang et al. |
| 6,284,264 | B1 | 9/2001 | Zerbe et al. |
| 6,306,437 | B1 | 10/2001 | El-Rashidy et al. |
| 6,316,027 | B1 * | 11/2001 | Johnson ............... A61K 9/0056 424/464 |
| 6,375,963 | B1 | 4/2002 | Repka et al. |
| 6,486,207 | B2 | 11/2002 | Yeager et al. |
| 6,488,953 | B2 | 12/2002 | Halliday et al. |
| 6,552,024 | B1 | 4/2003 | Chen et al. |
| 6,566,368 | B2 | 5/2003 | El-Rashidy et al. |
| 6,667,056 | B2 | 12/2003 | Chiesi et al. |
| 6,756,407 | B2 | 6/2004 | Heaton et al. |
| 6,974,590 | B2 | 12/2005 | Pather et al. |
| 7,037,526 | B1 | 5/2006 | Krumme et al. |
| 7,087,240 | B1 | 8/2006 | Fotinos |
| 7,332,230 | B1 | 2/2008 | Krumme |
| 7,357,891 | B2 | 4/2008 | Yang et al. |
| 7,374,782 | B2 | 5/2008 | Brown |
| 7,425,292 | B2 | 9/2008 | Yang et al. |
| 7,579,019 | B2 | 8/2009 | Tapolsky et al. |
| 7,666,337 | B2 | 2/2010 | Yang et al. |
| 7,824,588 | B2 | 11/2010 | Yang et al. |
| 7,897,080 | B2 | 3/2011 | Yang et al. |
| 7,910,031 | B2 | 3/2011 | Yang et al. |
| 7,910,641 | B2 | 3/2011 | Myers |
| 8,017,150 | B2 | 9/2011 | Yang et al. |
| 8,414,922 | B2 | 4/2013 | Bryson et al. |
| 8,603,514 | B2 | 12/2013 | Yang et al. |
| 8,652,378 | B1 | 2/2014 | Yang et al. |
| 8,658,201 | B2 | 2/2014 | Singh et al. |
| 8,663,687 | B2 | 3/2014 | Myers et al. |
| 8,685,437 | B2 | 4/2014 | Yang et al. |
| 8,765,167 | B2 | 7/2014 | Myers et al. |
| 8,846,074 | B2 | 9/2014 | Bryson et al. |
| 9,044,475 | B2 | 6/2015 | Giovinazzo et al. |
| 9,283,219 | B2 | 3/2016 | Bryson et al. |
| 9,427,412 | B2 | 8/2016 | Bryson et al. |
| 9,669,018 | B2 | 6/2017 | Giovinazzo et al. |
| 9,669,019 | B2 | 6/2017 | Giovinazzo et al. |
| 9,669,020 | B2 | 6/2017 | Giovinazzo et al. |
| 9,669,021 | B2 | 6/2017 | Giovinazzo et al. |
| 9,855,221 | B2 | 1/2018 | Myers et al. |
| 9,931,305 | B2 | 4/2018 | Yang et al. |
| 2001/0006677 | A1 | 7/2001 | McGinity et al. |
| 2003/0022912 | A1 | 1/2003 | Martino et al. |
| 2003/0073715 | A1 | 4/2003 | El-Rashidy et al. |
| 2003/0096012 | A1 | 5/2003 | Besse et al. |
| 2003/0107149 | A1 | 6/2003 | Yang et al. |
| 2004/0028613 | A1 | 2/2004 | Quay |
| 2004/0204440 | A1 | 10/2004 | Staniforth et al. |
| 2005/0031677 | A1 * | 2/2005 | Pather ............... A61K 9/0034 424/448 |
| 2005/0037055 | A1 | 2/2005 | Yang et al. |
| 2005/0226823 | A1 | 10/2005 | Krumme et al. |
| 2006/0141032 | A1 | 6/2006 | Larsen |
| 2006/0198873 | A1 | 9/2006 | Chan et al. |
| 2006/0210610 | A1 * | 9/2006 | Davidson ............ A61K 9/0056 424/439 |
| 2007/0149479 | A1 | 6/2007 | Fischer et al. |
| 2007/0149731 | A1 | 6/2007 | Myers |
| 2008/0008753 | A1 | 1/2008 | Singh |
| 2008/0057087 | A1 | 3/2008 | Krumme |
| 2008/0119504 | A1 | 5/2008 | Wikstrom et al. |
| 2008/0124381 | A1 | 5/2008 | Barnhart et al. |
| 2009/0023766 | A1 | 1/2009 | Clarke |
| 2010/0035886 | A1 | 2/2010 | Cincotta et al. |
| 2011/0033542 | A1 | 2/2011 | Myers et al. |
| 2011/0111011 | A1 | 5/2011 | Giovinazzo et al. |
| 2012/0195955 | A1 | 8/2012 | Bryson et al. |
| 2013/0064822 | A1 | 3/2013 | Ye et al. |
| 2013/0337148 | A1 | 12/2013 | Yang et al. |
| 2014/0377329 | A1 | 12/2014 | Bryson et al. |
| 2015/0216859 | A1 | 8/2015 | Giovinazzo et al. |
| 2016/0081914 | A1 | 3/2016 | Giovinazzo et al. |
| 2016/0089328 | A1 | 3/2016 | Giovinazzo et al. |
| 2016/0089367 | A1 | 3/2016 | Giovinazzo et al. |
| 2016/0095851 | A1 | 4/2016 | Giovinazzo et al. |
| 2016/0101101 | A1 | 4/2016 | Giovinazzo et al. |
| 2017/0035689 | A1 | 2/2017 | Myers et al. |

FOREIGN PATENT DOCUMENTS

| | | |
|---|---|---|
| CN | 1271276 A | 10/2000 |
| CN | 1460476 A | 12/2003 |
| DE | 19652268 A1 | 6/1998 |
| JP | H08-34731 A | 2/1996 |
| JP | 2001-506612 A | 5/2001 |
| JP | 2002-531393 A | 9/2002 |
| JP | 2004-520389 A | 7/2004 |
| JP | 2004-534839 A | 11/2004 |
| JP | 2004-535361 A | 11/2004 |
| JP | 2005-263704 A | 9/2005 |
| JP | 2006-508060 A | 3/2006 |
| JP | 2006508122 A | 3/2006 |
| JP | 2006523703 A | 10/2006 |
| JP | 2007-517053 A | 6/2007 |
| JP | 2008-540392 A | 11/2008 |
| JP | 2009-521532 A | 6/2009 |
| JP | 5760295 B2 | 8/2015 |
| JP | 2016-147882 A | 8/2016 |
| KR | 2000-0057627 A | 9/2000 |
| KR | 2008-0016608 A | 2/2008 |
| RU | 2189226 C2 | 9/2002 |
| RU | 2283650 C1 | 9/2006 |
| WO | WO-93/25168 A1 | 12/1993 |
| WO | WO-96/41619 A1 | 12/1996 |
| WO | WO-97/06786 A1 | 2/1997 |
| WO | WO-98/26763 A1 | 6/1998 |

(56) References Cited

FOREIGN PATENT DOCUMENTS

| WO | WO-98/48781 A1 | 11/1998 |
|----|----------------|---------|
| WO | WO-00/32171 A2 | 6/2000 |
| WO | WO-00/042992 A2 | 7/2000 |
| WO | WO-02/056808 A1 | 7/2002 |
| WO | WO-02/062315 A1 | 8/2002 |
| WO | WO-02/100377 A1 | 12/2002 |
| WO | WO-03/000018 A2 | 1/2003 |
| WO | WO-03/005944 A1 | 1/2003 |
| WO | WO-2004/026309 A1 | 4/2004 |
| WO | WO-2004/045537 A2 | 6/2004 |
| WO | WO-2004/066986 A1 | 8/2004 |
| WO | WO-2005/018323 A1 | 3/2005 |
| WO | WO-2005/065318 A2 | 7/2005 |
| WO | WO-2006/031209 A1 | 3/2006 |
| WO | WO-2006/039264 A1 | 4/2006 |
| WO | WO-2006/120412 A1 | 11/2006 |
| WO | WO-2007/030754 A2 | 3/2007 |
| WO | WO-2007/067494 A1 | 6/2007 |
| WO | WO-2007/075422 A2 | 7/2007 |
| WO | WO-2008/011194 A2 | 1/2008 |
| WO | WO-2008/039737 A2 | 4/2008 |
| WO | WO-2008/040534 A2 | 4/2008 |
| WO | WO-2008/100375 A2 | 8/2008 |
| WO | WO-2009/052421 A1 | 4/2009 |
| WO | WO-2010/144817 A1 | 12/2010 |
| WO | WO-2011/143424 A1 | 11/2011 |
| WO | WO-2014/049140 A1 | 4/2014 |

OTHER PUBLICATIONS

Chapter 55: Pharmaceutical Necessities and Chapter 57: Drug Absorption, Action, and Dispositon. Remington: The Science and Practice of Pharmacy. Gennaro, 1015, 1098-1126 (2000) (33 pages).

Chapter 9:Basic Biopharmaceutics of Buccal and Sublingual Absorption and Chapter 10: Chemical Enchancers in Buccal and Subligual Absorptions. *Enhancement in Drug Delivery*. Touitou and Barry, 175-213 (2007) (21 pages).

Communication enclosing the Extended European Search Report for European Patent Application No. 10786915.8, dated Oct. 12, 2012 (7 pages).

Declaration of Dr. Nathan Bryson Under 37 C.F.R. § 1.132 Traversing Grounds of Rejection for U.S. Appl. No. 12/813,820, dated Mar. 24, 2013 (6 pages).

Del Consuelo, "Ex vivo evaluation of bioadhesive films for buccal delivery of fentanyl," J Control Release. 122(2):135-40 (2007).

Design and Evaluation of Oral Administration Formulations, 1995, p. 199 (2 pages).

English translation of Indonesian Substantive Examination Report Stage I for Indonesian Application No. W00201103305, dated Jun. 5, 2014 (1 page).

English translation of Office Action for Japanese Patent Application No. 2012-515185, dated Jul. 8, 2014 (3 pages).

Eurasian Search Report for Eurasian Application No. 201270012, dated Jun. 25, 2012 (3 pages).

Examination Report for New Zealand Application No. 612686, dated Jun. 2, 2015 (2 pages).

Examination Report for New Zealand Application No. 612686, dated Mar. 25, 2014 (2 pages).

Extended European Search Report for European Application No. 11848299.1, dated Jun. 20, 2016 (14 pages).

Gandhi et al., "Oral cavity as a site for bioadhesive drug delivery," Adv Drug Deliv Rev. 13(1-2):43-74 (1994).

Goswami et al., "Sublingual drug delivery," Crit Rev Ther Drug Carrier Syst. 25(5):449-84 (2008).

Harris et al., "Drug delivery via the mucous membranes of the oral cavity," J Pharm Sci. 81(1):1-10 (1992).

International Preliminary Report on Patentability for International Application No. PCT/US2011/065665 dated Jun. 18, 2013 (11 pages).

International Search Report and Written Opinion for International Patent Application No. PCT/US11/65665, dated Apr. 23, 2012 (18 pages).

International Search Report and Written Opinion for PCT/US10/38336, dated Aug. 5, 2010 (16 pages).

Koller et al "Other formulations and future considerations for apomorphine for subcutaneous injection therapy," Neurology. 62(6 Suppl 4):S22-S26 (2004).

Lees et al., "Sublingual apomorphine and Parkinson's disease," J Neurol Neurosurg Psychiatry. 52(12):1440 (1989) (2 pages).

Montastruc et al., "Sublingual apomorphine in Parkinson's disease: a clinical and pharmacokinetic study," Clin Neuropharmacol. 14(5):432-437 (1991).

Notice of Opposition for European Patent No. EP2442650, dated May 26, 2016 (25 pages).

Notice of Opposition for European Patent No. EP2442650, dated May 27, 2016 (37 pages).

Notice of Reason for Rejection for Japanese Application No. 2013-544855, dated Feb. 10, 2015 (3 pages).

Notice of Reasons for Rejection for Japanese Application No. 2015-104145, dated Apr. 19, 2016 (5 pages).

Office Action for Chinese Application No. 201180067683.7, dated Feb. 25, 2015 (7 pages).

Office Action for Chinese Application No. 201180067683.7, dated Jul. 21, 2015 (5 pages).

Office Action for Chinese Application No. 2011800676837, dated Jun. 5, 2014 (English translation included) (21 pages).

Office Action for Israeli Application No. 226962, dated May 3, 2015 (10 pages).

Office Action for Korean Application No. 10-2012-7000835, dated Jun. 26, 2014 (English Translation included) (11pages).

Office Action for U.S. Appl. No. 14/962,806, dated Jun. 16, 2016 (13 pages).

Office Action for U.S. Appl. No. 14/963,835, dated Jun. 17, 2016 (11 pages).

Office Action for U.S. Appl. No. 14/963,910, dated Jun. 23, 2016 (15 pages).

Office Action for U.S. Appl. No. 14/963,971, dated Jun. 21, 2016 (16 pages).

Office Action for U.S. Appl. No. 14/971,532, dated Jun. 17, 2016 (20 pages).

Official Action for Eurasian Application No. 201390855, dated May 12, 2015 (4 pages).

Ondo et al., "Novel sublingual apomorphine treatment for patients with fluctuating Parkinson's disease," Movement Disorders. 14(4):664-8 (1999).

Ribaric, "The pharmacological properties and therapeutic use of apomorphine," Molecules. 17(5):5289-309 (2012).

Sam et al., "Stability of apomorphine in plasma and its determination by high-performance liquid chromatography with electrochemical detection," J Chromatogr B Biomed Appl. 658(2):311-7 (1994).

Sanchez et al., "Interplay of chromatographic parameters and analyte physical properties on retention and selectivity in hydrophilic interaction liquid chromatography," Phenomenex, Inc., (2007) (18 pages).

Semalty et al., "Formulation and characterization of mucoadhesive buccal films of glipizide," Indian J Pharm Sci. 70(1):43-8 (2008).

Substantive Examination Report Stage II for Indonesian Application No. W-00201303084 (4 pages).

Tan et al., "Functional COMT variant predicts response to high dose pyridoxine in Parkinson's disease," Am J Med Genet B Neuropsychiatr Genet. 137B(1):1-4 (2005).

Tsai et al., "Oral apomorphine delivery from solid lipid nanoparticles with different monostearate emulsifiers: pharmacokinetic and behavioral evaluations," J Pharm Sci. 100(2):547-557 (2011).

Van Laar et al., "A new sublingual formulation of apomorphine in the treatment of patients with Parkinson's disease," Mov Disord. 11(6):633-8 (1996).

Weast (ed.), *CRC Handbook of Chemistry and Physics 52nd Edition*. The Chemical Rubber Company (1971) (p. D-119).

Ying Kin et al., "Stability of apomorphine hydrochloride in aqueous sodium bisulphite solutions," Prog Neuropsychopharmacol Biol Psychiatry. 25(7):1461-8 (2001).

(56) References Cited

OTHER PUBLICATIONS

"Cynapsus Receives FDA Fast Track Designation for APL-130277 for the Treatment of OFF Episodes in Patients with Parkinson's Disease," Globe Newswire, available <https://globenewswire.com/news-release/2016/08/29/867552/0/en/Cynapsus-Receives-FDA-Fast-Track-Designation-for-APL-130277-for-the-Treatment-of-OFF-Episodes-in-Patients-with-Parkinson-s-Disease.html>, dated Aug. 29, 2016 (3 pages).
"Fast Track," available <http://www.fda.gov/ForPatients/Approvals/Fast/ucm405399.htm>, accessed Oct. 28, 2016 (2 pages).
"Sunovion Pharmaceuticals to Acquire Cynapsus Therapeutics," dated Aug. 31, 2016 (6 pages).
Ahlskog et al., "Frequency of levodopa-related dyskinesias and motor fluctuations as estimated from the cumulative literature," Mov Disord. 16(3):448-58 (2001).
Ang et al., "Stability of apomorphine in solutions containing selected antioxidante agents," Drug Des Devel Ther. 10:3253-65 (2016).
APO-go Ampoules 10mg/ml Package Leaflet, Feb. 2013 (2 pages).
Apokyn Prescribing information, Britannia Pharmaceuticals Limited, available <http://www.apokyn.com/assets/APOKYN_PI.pdf>, 2004 (16 pages).
Aquino et al., "Clinical spectrum of levodopa-induced complications," Mov Disord. 30(1):80-9 (2015).
Amy, The Pyridine and Quinoline Derivatives. *Principles of Pharmacy*. W. B. Saunders, p. 823 (1917).
Bhidayasiri et al., "Effective delivery of apomorphine in the management of Parkinson disease: practical considerations for clinicians and Parkinson nurses," Clin Neuropharmacol. 38(3):89-103 (2015).
Burkman, "Some kinetic and thermodynamic characteristics of apomorphine degradation," J Pharm Sci. 54:326-6 (1965).
Chapuis et al., "Impact of the motor complications of Parkinson's disease on the quality of life," Mov Disord. 20(2):224-30 (2005).
Cohn et al., "The measurement of the acidity of bread," J Biol Chem. 36:581-6 (1918).
Cotzias et al., "Similarities between neurologic effects of L-dopa and of apomorphine," N Engl J Med. 282(1):31-3 (1970).
Decker et al., "A stable parenteral solution of apomorphine," Clin Toxicol. 18(7):763-72 (1981).
Declaration of Dr. Nathan Bryson Under 37 C.F.R. § 1.132 Traversing Grounds of Rejection for U.S. Appl. No. 13/445,656, dated Sep. 24, 2012 (10 pages).
Declaration of Dr. Thierry Bilbault, dated Jan. 15, 2017 (14 pages).
Deffond et al., "Apomorphine in treatment of Parkinson's disease: comparison between subcutaneous and sublingual routes," J Neurol Neurosurg Psychiatry. 56(1):101-3 (1993).
Durif et al., "Apomorphine and diphasic dyskinesia," Clin Neuropharmacol. 17(1):99-102 (1994).
HBM Pharma/Biotech M&A Report 2016, Jan. 2016 (16 pages).
Holloway et al., "Pramipexole vs levodopa as initial treatment for Parkinson disease: a 4-year randomized controlled trial," Arch Neurol. 61(7):1044-53 (2004) (11 pages).
Hornykiewicz, "Basic research on dopamine in Parkinson's disease and the discovery of the nigrostriatal dopamine pathway: the view of an eyewitness," Neurodegener Dis. 5(3-4):114-7 (2008).
Hughes et al., "Sublingual apomorphine in the treatment of Parkinson's disease complicated by motor fluctuations," Clin Neuropharmacol. 14(6):556-61 (1991).
Kaul et al., "Auto-oxidation of apomorphine," J Pharm Sci. 50(3):266-7 (1961).
López et al., "Motor complications in Parkinson's disease: ten year follow-up study," Mov Disord. 25(16):2735-9 (2010).
Michael J Fox Foundation, MJFF Off Time Survey, "Executive Summary: Survey of Parkinson's Patients and Their Off Time Experience" (2 pages).
Michael J Fox Foundation, MJFF Survey—OFF Time Survey Results, "Impact of Parkinson's Disease Off Episodes," Aug. 11, 2014 (13 pages).
Notice of Allowance for U.S. Appl. No. 13/445,656, dated Dec. 13, 2012 (17 pages).
Notice of Allowance for U.S. Appl. No. 13/858,638, dated Aug. 8, 2014 (23 pages).
Notice of Allowance for U.S. Appl. No. 14/478,975, dated Nov. 3, 2015 (32 pages).
Notice of Allowance for U.S. Appl. No. 15/014,655, dated Jul. 19, 2016 (34 pages).
Notice of Final Rejection for Korean Application No. 10-2015-7016545, dated Sep. 5, 2016 (8 pages).
Oertel et al., "Pergolide versus levodopa monotherapy in early Parkinson's disease patients: The PELOMPET study," Mov Disord 21(3):343-53 (2006).
Office Action for Japanese Application No. 2015-104145, dated Dec. 6, 2016 (2 pages).
Office Action for U.S. Appl. No. 13/858,638, dated Jul. 3, 2013 (10 pages).
Office Action for U.S. Appl. No. 13/858,638, dated Sep. 6, 2013 (22 pages).
Official Action for Eurasian Application No. 201390855, dated Apr. 5, 2017 (5 pages).
Official Action for Japanese Application No. 2016-047759, dated Jan. 31, 2017 (4 pages).
Olanow et al., "Factors predictive of the development of Levodopa-induced dyskinesia and wearing-off in Parkinson's disease," Mov Disord. 28(8):1064-71 (2013).
Ondo et al., "Apomorphine injections: predictors of initial common adverse events and long term tolerability," Parkinsonism Relat Disord. 18(5):619-22 (2012).
Ondo et al., "Efficacy and tolerability of a novel sublingual apomorphine preparation in patients with fluctuating Parkinson's disease," Clin Neuropharmacol. 22(1):1-4 (1999).
Rascol et al., "A five-year study of the incidence of dyskinesia in patients with early Parkinson's disease who were treated with ropinirole or levodopa," N Engl J Med. 342(20):1484-91 (2000).
Reply to Office Action for U.S. Appl. No. 13/445,656, dated Sep. 24, 2012 (18 pages).
Reply to Office Action for U.S. Appl. No. 13/858,638, dated Feb. 6, 2014 (10 pages).
Response to Office Action for U.S. Appl. No. 13/853,290, dated Mar. 24, 2016 (17 pages).
Response to Restriction Requirement for U.S. Appl. No. 13/858,638, dated Aug. 1, 2013 (1 page).
Rizos et al., "Characterizing motor and non-motor aspects of early-morning off periods in Parkinson's disease: an international multicenter study," Parkinsonism Relat Disord. 20(11):1231-5 (2014).
Skoog et al., Theory of Neutralization Titrations. Fundamentals of Analytical Chemistry. 7:202 (1996).
Summons to attend oral proceedings pursuant to Rule 115(1) EPC for European Patent No. 2442650, dated Mar. 20, 2017 (15 pages).
Supplemental Amendment for U.S. Appl. No. 13/445,656, dated Nov. 20, 2012 (5 pages).
Tanner et al., "Epidemiology of Parkinson's disease," Neurol Clin. 14(2):317-35 (1996).
Wilcox et al., "Stability of apomorphine in solutions containing ascorbic acid and bisulfite and effects of antioxidants on apomorphine-induced cage climbing and hypothermia in mice," J Pharm Sci. 69(8):974-6 (1980).
Wüllner et al., "Requirements for Parkinson's disease pharmacotherapy from the patients' perspective: a questionnaire-based survey," Curr Med Res Opin. 28(7):1239-46 (2012).
Annexes I-III, Product Information for Ixense, European Medicines Agency, London, United Kingdom, 2004 (27 pages).
Examination Report for Australian Application No. 2017200331, dated Dec. 15, 2017 (3 pages).
Reproductive Health Drugs Advisory Committee, Urology Subcommittee, FDA Briefing Package, Apr. 10, 2000 (18 pages).
Communication pursuant to Article 94(3) EPC for European Patent Application No. 11848299.1, dated Mar. 15, 2018 (11 pages).
Examination Report for Indian Patent Application No. 6289/DELNP/2013, dated Mar. 12, 2019 (6 pages).

* cited by examiner

SUBLINGUAL FILMS

CROSS REFERENCE TO RELATED APPLICATIONS

This application is a continuation of U.S. patent application Ser. No. 13/858,638, filed Apr. 8, 2013, which is a continuation of U.S. patent application Ser. No. 13/445,656, filed Apr. 12, 2012, now U.S. Pat. No. 8,414,922, which is a continuation of International Patent Application No. PCT/US2011/05665, filed Dec. 16, 2011, which claims the benefit of U.S. Provisional Application No. 61/483,864, filed May 9, 2011, and U.S. Provisional Application No. 61/423,858, filed Dec. 16, 2010. Each of the aforementioned disclosures are incorporated herein by reference in their entirety.

BACKGROUND OF THE INVENTION

The invention relates to compositions including a dopamine agonist formulated for sublingual administration and the use of such compositions for the treatment of Parkinson's disease.

Parkinson's disease (PD) is a progressive degenerative disease of the central nervous system. The risk of developing Parkinson's disease increases with age, and afflicted individuals are usually adults over 40. Parkinson's disease occurs in all parts of the world, and affects more than 1.5 million individuals in the United States alone.

While the primary cause of Parkinson's disease is not known, it is characterized by degeneration of dopaminergic neurons of the substantia nigra. The substantia nigra is a portion of the lower brain, or brain stem that helps control voluntary movements. The shortage of dopamine in the brain caused by the loss of these neurons is believed to cause the observable disease symptoms.

The symptoms of PD vary from patient to patient. The most common symptom is a paucity of movement and rigidity, characterized by an increased stiffness of voluntary skeletal muscles. Additional symptoms include resting tremor, bradykinesia (slowness of movement), poor balance, and walking problems. Common secondary symptoms include depression, sleep disturbance, dizziness, stooped posture, dementia, problems with speech, breathing, and swallowing. The symptoms become progressively worse with time and ultimately result in death.

A variety of therapeutic treatments for PD are available. Perhaps the best known is levodopa, a dopamine precursor. While levodopa administration can result in a dramatic improvement in symptoms, patients can experience serious side-effects, including nausea and vomiting. Concurrent carbidopa administration with levodopa is a significant improvement, with the addition of carbidopa inhibiting levodopa metabolism in the gut, liver and other tissues, thereby allowing more levodopa to reach the brain. Other dopamine agonists, such as bromocriptine, pergolide, pramipexole, and andropinirole are also used to treat Parkinson's disease, and can be administered to PD patients either alone or in combination with levodopa.

Many patients develop involuntary choreiform movements which are the result of excessive activation of dopamine receptors. These movements usually affect the face and limbs and can become very severe. Such movements disappear if the dose of dopamine precursor (e.g., levodopa) or dopamine agonist is reduced, but this typically causes rigidity to return. Moreover, the margin between the beneficial and the unwanted effects appear to become progressively narrower as the period of chemotherapeutic treatment lengthens.

A further complication of long-term chemotherapeutic treatment with dopamine agonists is the development of rapid fluctuations in clinical state where the patient switches suddenly between mobility and immobility for periods ranging from a few minutes to a few hours. The fluctuations are of several general types. "Wearing-off" phenomena are deteriorations in the relief afforded by a dose of levodopa before the next dose takes effect (Van Laar T., CNS Drugs, 17:475 (2003)). Because they are related to a patient's dose schedule, such periods are often relatively predictable (Dewey R B Jr., Neurology, 62(suppl 4):S3-S7 (2004)). In contrast, "on-off" phenomena are sudden transitions from an "on" period of levodopa benefit to an "off" period of akinesia, rigidity, and tremor that occur in minutes or even seconds, (Swope D M., Neurology. 62(suppl 4):S27-S31 (2004)) with no discernible relation to a patient's dose schedule. Two other phenomena are the delayed "on" effect, in which levodopa's effects are substantially delayed, and dose failure (also known as the no-"on" or skipped-dose effect), in which no effects occur at all. These various "off" states can produce such an abrupt loss of mobility that the patient may suddenly stop while walking or be unable to rise from a chair in which he had sat down normally a few moments earlier.

Subcutaneous injections of apomorphine have proved to be effective in the treatment of "on-off" fluctuations in Parkinson's disease within 5 to 15 minutes, and last for 45 to 90 minutes. Trials have shown consistent reversal of "off" period akinesia, a decrease in daily levodopa requirements and consequently a decrease in the amount of "on" period dyskinesias. Advantages over other dopamine agonists include a quick onset of action and lower incidence of psychological complications. For a "rescue therapy" in patients with "on-off" fluctuations, apomorphine also has the advantage over other dopamine agonists that it has a relatively short half-life.

Numerous formulations and routes of administration for apomorphine have been studied and apomorphine therapy has been found to be hampered by various complications. For example, oral administration of apomorphine tablets has required high doses to achieve the necessary therapeutic effect because apomorphine administered by this route undergoes extensive metabolism in the small intestine and/or, upon absorption, in the liver; sublingual administration of apomorphine tablets caused severe stomatitis on prolonged use with buccal mucosal ulceration in half the patients treated (see Deffond et al., J. Neurol. Neurosurg. Psychiatry 56:101 (1993)); and intranasal administration produced transient nasal blockage, burning sensation and swollen nose and lips (see Koller et al., Neurology 62:S22 (2004)). While subcutaneous injections of apomorphine have proven effective, an injection by needle is difficult for Parkinson's patients because of impaired motor function. Furthermore, a common side effect of subcutaneous injection is the development of nodules, which often become infected, necessitating antiobiotic treatment or surgical debridement (see Prietz et al., J. Neurol. Neurosurg. Psychiatry 65:709 (1998)).

There is a need for new formulations of dopamine agonists which are safe, effective, and easy for a Parkinson's patient to use.

SUMMARY OF THE INVENTION

The invention features sublingual formulations including a dopamine agonist, or a salt thereof. The formulations can be useful for the treatment of Parkinson's disease, tremors, restless leg syndrome, sexual dysfunction, and depressive disorders therewith.

In one aspect, the invention features a pharmaceutical composition in unit dosage form formulated for sublingual administration, wherein the unit dosage form is a film including one or more disintegrants (e.g., materials that favor disintegration or fast dissolution by virtue of their solubility in water, such as hydrolyzed starches, sugars, and glycerin, which may play a dual role as a plasticizer and disintegrant) and a plasticizing agent, the film having a first portion including apomorphine hydrochloride, and a second portion including pH neutralizing agent, wherein the unit dosage form includes from 0.5 to 5 mg, from 4 to 10 mg, or from 8 to 20 mg of apomorphine hydrochloride and the pH neutralizing agent is present in an amount sufficient to produce a solution having a pH of between 3.0 and 6.0, preferably between 4.5 and 6.5, (e.g., a pH of between 2.5 and 4.5, 3.0 and 6.0, 3.5 and 6.5, 4.5 and 6.5, or 5.0 and 6.0) when the unit dosage form is placed in unbuffered water at pH 7 (e.g., the pH observed within 5 minutes of placing the unit dosage form in 1, 5, or 10 mL of unbuffered water). The film can include from 1 to 50% (w/w) (e.g., 1±0.75%, 2±1.5%, 3±0.5%, 5±2%. 7.5±2.5%, 10±2%. 14±3%, 18±4%, 22±5%, 25±5%, 30±5%. 35±5%, 40±5%, 45±5%, or 50±5% (w/w)) of the one or more disintegrants. In certain embodiments, the unit dosage form further includes a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose. In other embodiments, the unit dosage form further includes a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose. The pH neutralizing agent can be an organic base (e.g., pyridoxine, meglumine, or any organic base described herein) or an inorganic base (e.g., magnesium hydroxide, sodium bicarbonate, or an inorganic base described herein). In particular embodiments, the unit dosage form includes 35±5% (w/w) disintegrant, from 0.5 to 5 mg, from 4 to 10 mg, or from 8 to 20 mg of apomorphine hydrochloride and pyridoxine present in an amount sufficient to produce a solution having a pH of between 4.5 and 6.5 when the unit dosage form is placed in unbuffered water at pH 7.

In a related aspect, the invention features a pharmaceutical composition in unit dosage form formulated for sublingual administration, wherein the unit dosage form is a film including: (i) apomorphine hydrochloride; (ii) a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose; and (iii) a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose, wherein the unit dosage form includes from 0.5 to 5 mg, from 4 to 10 mg, or from 8 to 20 mg of apomorphine hydrochloride.

The invention further features a pharmaceutical composition in unit dosage form formulated for sublingual administration, wherein the unit dosage form is a bilayer film having a first layer and a second layer, the second layer including a pH neutralizing agent and the first layer including: (i) apomorphine hydrochloride; (ii) a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose; and (iii) a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose, wherein the unit dosage form includes from 0.5 to 5 mg, from 4 to 10 mg, or from 8 to 20 mg of apomorphine hydrochloride and the pH neutralizing agent is present in an amount sufficient to produce a solution having a pH of between 3.0 and 6.0, preferably between 4.5 and 6.5, (e.g., a pH of between 2.5 and 4.5, 3.0 and 6.0, 3.5 and 6.5, 4.5 and 6.5, or 5.0 and 6.0) when the unit dosage form is placed in unbuffered water at pH 7 (e.g., the pH observed within 5 minutes of placing the unit dosage form in 1, 5, or 10 mL of unbuffered water). The pH neutralizing agent can be an organic base (e.g., pyridoxine, meglumine, or any organic base described herein) or an inorganic base (e.g., magnesium hydroxide, sodium bicarbonate, or an inorganic base described herein). In particular embodiments, the unit dosage form includes an antioxidant, 1±0.5% (w/w) glycerol monostereate, 35±5% (w/w) disintegrant, from 0.5 to 5 mg, from 4 to 10 mg, or from 8 to 20 mg of apomorphine hydrochloride and pyridoxine present in an amount sufficient to produce a solution having a pH of between 4.5 and 6.5 when the unit dosage form is placed in unbuffered water at pH 7.

In one embodiment of any of the above unit dosage forms, the unit dosage form can include from 0.2 to 5% (w/w) e.g., 0.5±0.25%, 0.75±0.25%. 1±0.5%. 1.5±0.5%. 2±0.5%, 2.5±0.5%, 3±0.5%, 3.5±0.5%, 4±0.5%, or 5±0.5% (w/w)) of a permeation enhancer (e.g., an ionic surfactant, nonionic surfactant, polysorbate, derivatives of tocopherol, poloxamer, monoglyceride, diglyceride, fatty acid, fatty alcohol, mixtures thereof, or any permeation enhancer described herein). In particular embodiments, the permeation enhancer is glycerol monostereate. In another embodiment of any of the above unit dosage forms, the unit dosage form can include an antioxidant (e.g., from 0.05 to 2.5% (w/w) (e.g., 0.05±0.025%, 0.1±0.075%, 0.3±0.1%, 0.5±0.25%, 0.75±0.25%, 1±0.5%. 1.5±0.5%. 2±0.5%, or 2.5±0.5% (w/w)) metabisulfite, or any antioxidant described herein. In certain embodiments of the above unit dosage forms, the unit dosage form can further include from 3 to 18% (w/w) (e.g., 3 to 12%, 3±1%, 5±2%, 7.5±2.5%, 10±3%, 12±3%. 15±3%, or 18±3% (w/w)) plasticizing agent, such as a polyol (e.g., sorbitol, mannitol, maltitol, xylitol, glycerol, propylene glycol, or polyethylene glycol), oleic acid, or triacetin. In particular embodiments of the above unit dosage forms, the unit dosage form can include from 1 to 50% (w/w) (e.g., 1±0.75%, 2±1.5%, 3±0.5%, 5±2%, 7.5±2.5%, 10±2%. 14±3%, 18±4%, 22±5%. 25±5%, 30±5%, 35±5%. 40±5%, 45±5%, or 50±5% (w/w)) hydrolyzed starch. The hydrolyzed starch can be a dextrin, a maltodextrin, or any hydrolyzed starch described herein. In still another embodiment of any of the unit dosage forms of the invention, the unit dosage form can have a sublingual bioavailability of greater than 40% (e.g., a sublingual bioavailability of from 40 to 70%. 45 to 85%. 55 to 95%, 65 to 100%. 70 to 100%, 70 to 99%, 75 to 100%. 75 to 99%, or 80 to 99%). In particular embodiments, any of the unit dosage forms described herein can have a $T_{max}$ of from 10 to 25 minutes (e.g., 9±3, 10±3, 11±3, 12±3, 13±3, 14±3, 15±3, 16±3, 17±3, 18±3, 20±3, 22±3, 24±3, or 25±3 minutes). In still another embodiment of any of the above unit dosage forms, the unit dosage form, following sublingual administration to a subject, produces an average circulating apomorphine concentration of at least 3 ng/mL within a period of from 5 to 15 minutes following the administration. For example, the unit dosage form can produce an average circulating concentration of from 3 to 6 ng/mL within 7 to 10 minutes, from 5 to 10 ng/mL within 5 to 10 minutes, from 7 to 12 ng/mL within 5 to 10 minutes, from 10 to 16 ng/mL within 5 to 10 minutes, from 3 to 6 ng/mL within 7 to 15 minutes, from 5 to 10 ng/mL within 7 to 15 minutes, from 7 to 12 ng/mL within 7 to 15 minutes, from 10 to 16 ng/mL within 7 to 15 minutes, from 3 to 6 ng/mL within 15 to 20 minutes, from 5 to 10 ng/mL within 15 to 20 minutes, 30 from 7 to 12 ng/mL within 15 to 20 minutes, or from 10 to 16 ng/mL within 15 to 20 minutes following the administration. In one embodiment of any of the above unit dosage forms, the unit dosage form when administered sublingually to a subject is non-irritating (e.g., non-irritating using the test of Example 7). In one particular embodiment of any of the above unit dosage forms, the unit dosage form is an individual film packaged in a sealed plastic-lined aluminum foil, wherein the unit dosage form is stable for a period of at least 2 months, 4 months, or 6 months at 40° C. (e.g., uncolored using the test described in Example 8).

The invention features a pharmaceutical composition in unit dosage form formulated for sublingual administration, the unit dosage form having a first portion including an acid addition salt of a dopamine agonist, and a second portion including a pH neutralizing agent, wherein the dopamine agonist is selected from bromocriptine, cabergoline, dihydroergocryptine, lisuride, piribedil, pergolide, pramipexole, rotigotine, ropinirol, and acid addition salts thereof. In particular embodiments, the unit dosage form is a lozenge, a pill, a tablet, a film, or a strip.

The invention features a pharmaceutical composition in unit dosage form formulated for sublingual administration, wherein the unit dosage form is a film including: (i) from 10 to 75% (w/w) (e.g., 30 to 75%, 10±5%. 15±5%. 20±5%, 25±5%. 30±5%. 35±5%, 40±5%. 45±5%. 50±5%, 55±5%, 60±5%, 65±5%, 70±5%, or 75±5% (w/w)) dopamine agonist, or an acid addition salt thereof; (ii) from 0.5 to 16% (w/w) (e.g., 0.5 to 10%, 0.5±0.1%, 1±0.5%, 2±0.75%. 3±1%. 5±1%. 6±2%, 7±3%. 8±3%, 9±3%, 12±3%, or 16±3% (w/w)) of a low molecular weight polymer having a weight average molecular weight of from 5 KDa to 50 KDa (e.g., 5±3, 8±3, 10±3, 15±5, 18±5, 22±6, 28±6, 34±8, 44±8, or 50±10 KDa) selected from hydroxypropyl cellulose, hydroxypropyl methyl cellulose, hydroxyethyl cellulose, carboxymethyl cellulose, and methyl cellulose: and (iii) from 4 to 35% (w/w) (e.g., 4 to 20%. 4±2%, 5±2.5%. 7.5±3%. 10±3.5%, 14±5%. 18±5%. 20±6%, 25±6%. 30±6%, or 35 t 6% (w/w)) of a high molecular weight polymer having a weight average molecular weight of greater than 60 KDa (e.g., 60 KDa to 500 KDa, 60 KDa to 1,000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose. In certain embodiments the film has a surface coated with a pH neutralizing agent (e.g., a coating or dusting of an inorganic or organic base). In still other embodiments, the unit dosage form when placed in 1 mL of unbuffered water at pH 7 results in a solution having a pH of between 2.5 and 6.5, preferably between 4.5 and 6.5, (e.g., a pH of between 2.5 and 4.5, 3.0 and 6.0, 3.5 and 6.5, 4.5 and 6.5, or 5.0 and 6.0), and has a sublingual bioavailability of greater than 40% (e.g., a sublingual bioavailability of from 40 to 70%, 45 to 85%, 55 to 95%. 65 to 100%, 70 to 100%. 70 to 99%, 75 to 100%. 75 to 99%, or 80 to 99%). In particular embodiments, the dopamine agonist is selected from apomorphine, an apomorphine prodrug, bromocriptine, cabergoline, dihydroergocryptine, lisuride, piribedil, pergolide, pramipexole, rotigotine, ropinirol, and acid addition salts thereof.

In a related aspect, the invention features a pharmaceutical composition in unit dosage form formulated for sublingual administration, wherein the unit dosage form is a bilayer film having a first layer and a second layer, the first layer including: (i) from 10 to 75% (w/w) (e.g., 30 to 75%, 10±5%. 15±5%, 20±5%. 25±5%, 30±5%, 35±5%. 40±5%, 45±5%, 50±5%. 55±5%, 60±5%, 65±5%. 70±5%, or 75±5% (w/w)) dopamine agonist, or an acid addition salt thereof; (ii) from 0.5 to 16% (w/w) (e.g., 0.5 to 10%, 0.5±0.1%, 1±0.5%, 2±0.75%. 3±1%. 5±1%. 6±2%. 7±3%. 8±3%, 9±3%, 12±3%, or 16±3% (w/w)) of a low molecular weight polymer having a weight average molecular weight of from 5 KDa to 50 KDa (e.g., 5 3, 8±3, 10±3, 15±5, 18±5, 22±6, 28±6, 34±8, 44±8, or 50±10 KDa) selected from hydroxypropyl cellulose, hydroxypropyl methyl cellulose, hydroxyethyl cellulose, carboxymethyl cellulose, and methyl cellulose: and (iii) from 4 to 35% (w/w) (e.g., 4 to 20%, 4±2%, 5±2.5%, 7.5±3%, 10±3.5%. 14±5%, 18±5%, 20±6%. 25±6%, 30±6%, or 35±6% (w/w)) of a high molecular weight polymer having a weight average molecular weight of greater than 60 KDa (e.g., 60 KDa to 500 KDa, 60 KDa to 1.000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose, and wherein the second layer includes a pH neutralizing agent and from 15 to 50% (w/w) (e.g., 15±5%. 20±5%, 25±5%, 30±5%. 35±5%, 40±5%, 45±5%, or 50±5% (w/w)) of a high molecular weight polymer having a weight average molecular weight of greater than 60 KDa (e.g., 60 KDa to 500 KDa, 60 KDa to 1,000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose. In certain embodiments the second layer includes from 6 to 65% (w/w) (e.g., 10 to 50%. 6±12%, 8±12%, 10±2%, 14±3%. 18±4%, 22±5%, 25±5%. 30±5%, 35±5%. 40±5%. 45±5%, 50±5%. 55±5%. 60±5%, or 65±5% (w/w)) pH neutralizing agent. In particular embodiments, the unit dosage form is a trilayer film including two outer dopamine agonist layers, and one inner pH neutralizing layer. In particular embodiments, the dopamine agonist is selected from apomorphine, an apomorphine prodrug, bromocriptine, cabergoline, dihydroergocryptine, lisuride, piribedil, pergolide, pramipexole, rotigotine, ropinirol, and acid addition salts thereof. In particular embodiments, the unit dosage form includes an antioxidant. 1±0.5% glycerol monostereate, 35±5% (w/w) hydrolyzed starch, and 4±2% (w/w) pyridoxine, wherein the first layer includes 10±5% (w/w) apomorphine hydrochloride, 2±0.75% (w/w) of a low molecular weight polymer having a weight average molecular weight of from 5 KDa to 50 KDa, and 30±6% (w/w) of a high molecular weight polymer having a weight average molecular weight of greater than 60 KDa.

The invention features a pharmaceutical composition in unit dosage form formulated for sublingual administration, wherein the unit dosage form is a film including: (i) from 10 to 75% (w/w) (e.g., 30 to 75%, 10±5%, 15±5%. 20±5%, 25±5%, 30±5%. 35±5%, 40±5%, 45±5%. 50±5%, 55±5%, 60±5%. 65±5%, 70±5%, or 75±5% (w/w)) apomorphine, an apomorphine prodrug, or an acid addition salt thereof; (ii) from 0.5 to 16% (w/w) (e.g., 0.5 to 10%. 0.5±0.1%. 1±0.5%. 2±0.75%, 3±1%, 5±1%, 6±2%. 7±3%. 8±3%. 9±3%. 12±3%, or 16±3% (w/w)) of a low molecular weight polymer having a weight average molecular weight of from 5 KDa to 50 KDa (e.g., 5±3, 8±3, 10±3, 15±5, 18±5, 22±6, 28±6, 34±8, 44±8, or 50±10 KDa) selected from hydroxypropyl cellulose, hydroxypropyl methyl cellulose, hydroxyethyl cellulose, carboxymethyl cellulose, and methyl cellulose; and (iii) from 4 to 35% (w/w) (e.g., 4 to 20%. 4±2%. 5±2.5%. 7.5±3%. 10±3.5%, 14±5%, 18±5%. 20±6%, 25±6%. 30±6%, or 35±6% (w/w)) of a high molecular weight polymer having a weight average molecular weight of greater than 60 KDa (e.g., 60 KDa to 500 KDa, 60 KDa to 1.000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose. In certain embodiments the film has a surface coated with a pH neutralizing agent (e.g., a coating or dusting of an inorganic or organic base). In still other embodiments, the unit dosage form when placed in 1 mL of unbuffered water at pH 7 results in a solution having a pH of between 2.5 and 6.5, preferably between 4.5 and 6.5, (e.g., a pH of between 2.5 and 4.5, 3.0 and 6.0, 3.5 and 6.5, 4.5 and 6.5, or 5.0 and 6.0), and has a sublingual bioavailability of greater than 40% (e.g., a sublingual bioavailability of from 40 to 70%, 45 to 85%, 55 to 95%. 65 to 100%, 70 to 100%. 70 to 99%, 75 to 100%, 75 to 99%, or 80 to 99%).

In a related aspect, the invention features a pharmaceutical composition in unit dosage form formulated for sublingual administration, wherein the unit dosage form is a bilayer film having a first layer and a second layer, the first layer including: (i) from 10 to 75% (w/w) (e.g., 30 to 75%. 10±5%, 15±5%. 20±5%, 25±5%. 30±5%, 35±5%, 40±5%. 45±5%, 50±5%, 55±5%. 60±5%, 65±5%. 70±5%, or 75±5% (w/w)) apomorphine, an apomorphine prodrug, or an acid addition salt thereof; (ii) from 0.5 to 16% (w/w) (e.g., 0.5 to 10%, 0.5±0.1%, 1±0.5%, 2±0.75%, 3±1%, 5±1%, 6±2%, 7±3%. 8±3%. 9±3%. 12±3%, or 16±3% (w/w)) of a low molecular weight polymer having a weight average molecular weight of from 5 KDa to 50 KDa (e.g., 5±3, 8±3, 10±3, 15±5, 18±5, 22±6, 28±6, 34±8, 44±8, or 50±10 KDa) selected from hydroxypropyl cellulose, hydroxypropyl methyl cellulose, hydroxyethyl cellulose, carboxymethyl cellulose, and methyl cellulose: and (iii) from 4 to 35% (w/w) (e.g., 4 to 20%. 4±2%, 5±2.5%, 7.5±3%, 10±3.5%, 14±5%, 18±5%. 20±6%, 25±6%. 30±6%, or 35±6% (w/w)) of a high molecular weight polymer having a weight average molecular weight of greater than 60 KDa (e.g., 60 KDa to 500 KDa, 60 KDa to 1,000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose, and wherein the second layer includes a pH neutralizing agent and from 15 to 50% (w/w) (e.g., 15±5%. 20±5%. 25±5%, 30±5%, 35±5%, 40±5%. 45±5%, or 50±5% (w/w)) of a high molecular weight polymer having a weight average molecular weight of greater than 60 KDa (e.g., 60 KDa to 500 KDa, 60 KDa to 1.000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose. In certain embodiments the second layer includes from 6 to 65% (w/w) (e.g., 10 to 50%, 6±2%. 8±2%. 10±2%. 14±3%, 18±4%. 22±5%. 25±5%, 30±5%. 35±5%, 40±5%, 45±5%. 50±5%, 55±5%, 60±5%, or 65±5% (w/w)) pH neutralizing agent. In particular embodiments, the unit dosage form is a trilayer film including two outer apomorphine layers, and one inner pH neutralizing layer.

In certain embodiments of the above aspects, the film further includes from 3 to 18% (w/w) (e.g., 3 to 12%. 3±1%. 5±2%. 7.5±2.5%. 10±3%, 12±3%, 15±3%, or 18±3% (w/w)) plasticizing agent such as a polyol (e.g., sorbitol, mannitol, maltitol, xylitol, glycerol, propylene glycol, or polyethylene glycol), oleic acid, or triacetin.

In particular embodiments of the above aspects, the film, or one layer of the film, further includes from 1 to 50% (w/w) (e.g., 1±0.75%. 2±1.5%. 3±0.5%. 5±2%. 7.5±2.5%. 10±2%, 14±3%, 18±4%. 22±5%, 25±5%, 30±5%. 35±5%, 40±5%, 45±5%, or 50±5% (w/w)) hydrolyzed starch. The hydrolyzed starch can be a dextrin, a maltodextrin, or any hydrolyzed starch described herein.

The films of the invention can include an antioxidant. For example, the films, or one layer of a bilayer film can include from 0.05 to 2.5% (w/w) (e.g., 0.05±0.025%, 0.1±0.075%, 0.3±0.1%. 0.5±0.25%, 0.75±0.25%. 1±0.5%. 1.5±0.5%, 2±0.5%, or 2.5±0.5% (w/w)) metabisulfite, or any antioxidant described herein.

The films of the invention can have a $T_{max}$ of from 10 to 25 minutes (e.g., 9±3, 10±3, 11±3, 12±3.13±3, 14±3, 15±3, 16±3.17±3, 18±3, 20±3.22±3.24±3, or25±3 minutes).

The films of the invention can include from 0.2 to 5% (w/w) e.g., 0.5±0.25%, 0.75±0.25%. 1±0.5%. 1.5±0.5%. 2±0.5%, 2.5±0.5%, 3±0.5%, 3.5±0.5%, 4±0.5%, or 5±0.5% (w/w)) of a permeation enhancer (e.g., an ionic surfactant, nonionic surfactant, polysorbate, derivatives of tocopherol, poloxamer, monoglyceride, diglyceride, fatty acid, fatty alcohol, mixtures thereof, or any permeation enhancer described herein). In particular embodiments, the permeation enhancer is glycerol monostereate.

The films of the invention can include a low molecular weight polymer selected from hydroxypropyl methyl cellulose, hydroxypropyl cellulose, and hydroxyethyl cellulose. For example, the hydroxypropyl methylcellulose can have about 20% to about 35% methoxyl substitution and about 5% to about 15% hydroxypropyl substitution.

The films of the invention can include a high molecular weight polymer selected from hydroxypropyl methyl cellulose and hydroxyethyl cellulose. For example, the high molecular weight polymer can be hydroxypropyl methyl cellulose having about 20% to about 35% methoxyl substitution and about 5% to about 15% hydroxypropyl substitution. The high molecular weight polymer can be a hydroxyethyl cellulose having a weight average molecular weight of from 60 KDa to 1.000 KDa (e.g., 60 KDa to 500 KDa, 60 KDa to 1.000 KDa, 80 KDa to 120 KDa, 100 KDa to 300 KDa, 220 KDa to 500 KDa, or 400 KDa to 800 KDa).

In particular embodiments the first layer is separated from the second layer by a barrier (e.g., a third layer).

For films of the invention including a pH neutralizing agent, in certain embodiments the pH neutralizing agent is an inorganic base (e.g., aluminum hydroxide, aluminosilicates, calcium hydroxide, magnesium hydroxide, potassium hydroxide, sodium hydroxide, calcium carbonate, iron carbonate, magnesium carbonate, zinc carbonate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, mixtures thereof, and any inorganic base described herein). In still other embodiments, the pH neutralizing agent is an organic base (e.g., acetate salts, citrate salts, stearate salts, laurate salts, proprionate salts, lactate salts, succinate salts, oxalate salts, tartrate salts, glycolate salts, galacturonate salts, glucuronate salts, alginate salts, sorbate salts, caprylate salts, carboxymethyl cellulose, polyacrylate, and mixtures thereofand amines, such as pyridoxine, meglumine, lysine, Eudragit E, diethanolamine, glycine, citrate, acetate, histidine, N-methyl glucamine, and tris(hydroxymethyl)aminomethane, mixtures thereof, or any organic base described herein). In particular embodiments, the base has a pKa of from 2.5 to 9.5 (e.g., a pKa of 2±0.5, 2.5±1, 3±1.5, 4±2, 5±2, 6±2, 7±1, or a pKa of from 4.5 to 8.5).

In a related aspect, the invention features a kit including: (i) a monolayer film of the invention; (ii) a pH neutralizing agent; and (iii) instructions for administering the first film and the pH neutralizing agent simultaneously to a subject.

The sublingual formulations can include dopamine agonist particles having an effective particle size of from 0.5 μm to 50 μm (e.g., an effective particle size of from 1 μm to 10 μm. 1 μm to 9 μm, from 1 μm to 8 μm, from 1 μm to 7 μm, from 1 μm to 6 μm, from 1 μm to 5 μm, from 2 μm to 10 μm, from 3 μm to 10 μm, from 4 μm to 10 μm, from 2 μm to 7 μm. 2 μm to 6 μm, 0.5 μm to 25 μm, 0.5 μm to 20 μm, or from 5 μm to 12 μm). In particular embodiments, the formulations include dopamine agonist particles containing apomorphine, an apomorphine prodrug, bromocriptine, cabergoline, dihydroergocryptine, lisuride, piribedil, pergolide, pramipexole, rotigotine, ropinirol, or particles formed from their acid addition salts.

The sublingual formulations can include dopamine agonist particles having an effective particle size of from 10 μm to 100 μm (e.g., an effective particle size of from 10 μm to 90 μm, from 10 μm to 80 μm, from 10 μm to 70 μm, from 10 μm to 60 μm, from 10 μm to 50 μm, from 20 μm to 100 μm, from 30 μm to 100 μm, from 40 μm to 100 μm, from 20 μm to 70 μm, or from 20 μm to 60 μm). In particular embodiments, the formulations include dopamine agonist particles containing apomorphine, an apomorphine prodrug, bromocriptine, cabergoline, dihydroergocryptine, lisuride, piribedil, pergolide, pramipexole, rotigotine, ropinirol, or particles formed from their acid addition salts.

In certain other embodiments, the sublingual formulations can include dopamine agonist particles having an effective particle size of from 20 nm to 1 μm (e.g., an effective particle size of from 20 nm to 1 μm, from 40 nm to 1 μm, from 60 nm to 1 μm, from 80 nm to 1 μm, from 100 nm to 1 μm, from 20 nm to 800 nm, from 20 nm to 700 nm, from 50 nm to 700 nm, from 40 nm to 800 nm, from 60 nm to 800 nm, from 100 nm to 800 nm, from 60 nm to 700 nm, from 60 nm to 600 nm, from 100 nm to 600 nm, from 150 nm to 800 nm, or from 150 nm to 600 nm). In particular embodiments, the formulations include dopamine agonist particles containing apomorphine, an apomorphine prodrug, bromocriptine, cabergoline, dihydroergocryptine, lisuride, piribedil, pergolide, pramipexole, rotigotine, ropinirol, or particles formed from their acid addition salts.

The sublingual formulations can include apomorphine particles having an effective particle size of from 0.5 μm to 50 μm (e.g., an effective particle size of from 1 μm to 10 μm. 1 μm to 9 μm, from 1 μm to 8 μm, from 1 μm to 7 μm, from 1 μm to 6 μm, from 1 μm to 5 μm, from 2 μm to 10 μm, from 3 μm to 10 μm, from 4 μm to 10 μm, from 2 μm to 7 μm. 2 μm to 6 μm, 0.5 μm to 25 μm, 0.5 μm to 20 μm, or from 5 μm to 12 μm).

The sublingual formulations can include apomorphine particles having an effective particle size of from 10 μm to 100 μm (e.g., an effective particle size of from 10 μm to 90 μm, from 10 μm to 80 μm, from 10 μm to 70 μm, from 10 μm to 60 μm, from 10 μm to 50 μm, from 20 μm to 100 μm, from 30 μm to 100 μm, from 40 μm to 100 μm, from 20 μm to 70 μm, or from 20 μm to 60 μm).

In certain other embodiments, the sublingual formulations can include apomorphine particles having an effective particle size of from 20 nm to 1 μm (e.g., an effective particle size of from 20 nm to 1 μm, from 40 nm to 1 μm, from 60 nm to 1 μm, from 80 nm to 1 μm, from 100 nm to 1 μm, from 20 nm to 800 nm, from 20 nm to 700 nm, from 50 nm to 700 nm, from 40 nm to 800 nm, from 60 nm to 800 nm, from 100 nm to 800 nm, from 60 nm to 700 nm, from 60 nm to 600 nm, from 100 nm to 600 nm, from 150 nm to 800 nm, or from 150 nm to 600 nm).

In another aspect, the invention features a pharmaceutical composition in unit dosage form formulated for sublingual administration, the unit dosage form including from 2 to 60 mg of an apomorphine prodrug (e.g., from 2 to 15 mg, 10 to 50 mg, 12 to 30 mg, 20 to 50 mg, 15 to 30 mg, or 35 to 50 mg of an apomorphine prodrug) in the form of apomorphine particles having an effective particle size of from 10 μm to 100 μm (e.g., an effective particle size of from 10 μm to 90 μm, from 10 μm to 80 μm, from 10 μm to 70 μm, from 10 μm to 60 μm, from 10 μm to 50 μm, from 20 μm to 100 μm, from 30 μm to 100 μm, from 40 μm to 100 μm, from 20 μm to 70 μm, or from 20 μm to 60 μm). The unit dosage form can be a lozenge, a pill, a tablet, a film, or strip including from the apomorphine prodrug in its free base form. In still other embodiments, the unit dosage form is a film formulation described herein.

In still another aspect, the invention features a pharmaceutical composition in unit dosage form formulated for sublingual administration, the unit dosage form including dopamine agonist particles having an effective particle size of from 10 μm to 100 μm (e.g., an effective particle size of from 10 μm to 90 μm, from 10 μm to 80 μm, from 10 μm to 70 μm, from 10 μm to 60 μm, from 10 μm to 50 μm, from 20 μm to 100 μm, from 30 μm to 100 μm, from 40 μm to 100 μm, from 20 μm to 70 μm, or from 20 μm to 60 μm). The unit dosage form can be a lozenge, a pill, a tablet, a film, or strip includng from the dopamine agonist in its free base form. In still other embodiments, the unit dosage form is a film formulation described herein. In particular embodiments, the formulations include dopamine agonist particles containing apomorphine, an apomorphine prodrug, bromocriptine, cabergoline, dihydroergocryptine, lisuride, piribedil, pergolide, pramipexole, rotigotine, ropinirol, or particles formed from their acid addition salts.

In certain embodiments, the sublingual formulation includes apomorphine particle and the apomorphine particle include an acid addition salt of apomorphine or an apomorphine prodrug. The acid addition salt can be apomorphine hydrochloride or any acid addition salt described herein. Alternatively, the acid addition salt can be the hydrochloride salt of an apomorphine prodrug or any other acid addition salt described herein.

In an embodiment of any of the above pharmaceutical compositions, the pharmaceutical composition is in a unit dosage form including from 0.1 to 100 mg or 2 to 60 mg of apomorphine, an apomorphine prodrug, or an acid addition salt thereof (e.g., from 0.5 to 5 mg, 4 to 10 mg, 6 to 15 mg, 8 to 20 mg, 10 to 25 mg, 12 to 30 mg, 20 to 35 mg, 25 to 40 mg, or 30 to 40 mg of apomorphine, an apomorphine prodrug, or an acid addition salt thereof). For example, each unit dosage form can contain 1±0.5 mg, 3±1 mg, 4±1 mg, 5±1 mg, 8±2 mg, 10±13 mg, 12±3 mg, 15±13 mg, 22±4 mg, 27±4 mg, 30±5 mg, 35±5 mg, 40±5 mg, 45±5 mg, 50±5 mg, 55±5 mg, or 60±5 mg of apomorphine, an apomorphine prodrug, or an acid addition salt thereof.

In another embodiment of any of the above pharmaceutical compositions, the pharmaceutical composition is in a unit dosage form including an acid addition salt of ropinirol. In particular embodiments, the pharmaceutical composition includes the hydrochloride salt of ropinirol.

In another embodiment of any of the above pharmaceutical compositions, the pharmaceutical composition is a film including a solid solution of an acid addition salt of the dopamine agonist (e.g., a solid solution of apomorphine, an apomorphine prodrug, bromocriptine, cabergoline, dihydroergocryptine, lisuride, piribedil, pergolide, pramipexole, rotigotine, ropinirol, or an acid addition salt thereof).

In an embodiment of any of the above pharmaceutical compositions, the pharmaceutical composition is in a unit dosage form including from 0.1 to 100 mg or 0.1 to 40 mg of ropinirol, or an acid addition salt thereof (e.g., from 0.1 to 2 mg, 1 to 5 mg, 4 to 10 mg, 6 to 15 mg, 8 to 20 mg, 10 to 25 mg, 12 to 30 mg, 20 to 35 mg, 25 to 40 mg, or 30 to 40 mg of ropinirol, or an acid addition salt thereof). For example, each unit dosage form can contain 0.5±0.25 mg, 3±1 mg, 4±1 mg, 5±1 mg, 8±2 mg, 10±3 mg, 12±3 mg, 15±3 mg, 22±4 mg, 27±4 mg, 30±5 mg, 35±5 mg, or 40±5 mg, of ropinirol, or an acid addition salt thereof.

In an embodiment of any of the above pharmaceutical compositions, the pharmaceutical composition is in a unit dosage form including from 0.1 to 100 mg or 0.2 to 20 mg of bromocriptine, or an acid addition salt thereof (e.g., from 0.2 to 2 mg, 0.5 to 3 mg, 1 to 4 mg, 3 to 7 mg, 6 to 11 mg, 9 to 15 mg, 13 to 18 mg, or 16 to 20 mg of bromocriptine, or an acid addition salt thereof). For example, each unit dosage form can contain 0.2±0.1 mg, 0.5±0.25 mg, 1±0.5 mg, 2±0.5 mg, 3±1 mg, 4±1.5 mg, 6±2 mg, 10±3 mg, 14±3 mg, 18±3 mg, or 20±5 mg of bromocriptine, or an acid addition salt thereof.

In an embodiment of any of the above pharmaceutical compositions, the pharmaceutical composition is in a unit dosage form including from 0.1 to 100 mg or 2 to 20 mg of cabergoline, or an acid addition salt thereof (e.g., from 0.2 to 2 mg, 0.5 to 3 mg, 1 to 4 mg, 3 to 7 mg, 6 to 11 mg, 9 to 15 mg, 13 to 18 mg, or 16 to 20 mg of cabergoline, or an acid addition salt thereof). For example, each unit dosage form can contain 0.2±0.1 mg, 0.5±0.25 mg, 1±0.5 mg, 2±0.5 mg, 3±1 mg, 4±1.5 mg, 6±2 mg, 10±3 mg, 14±3 mg, 18±3 mg, or 20±5 mg of cabergoline, or an acid addition salt thereof.

In an embodiment of any of the above pharmaceutical compositions, the pharmaceutical composition is in a unit dosage form including from 0.1 to 100 mg or 0.5 to 30 mg of dihydroergocryptine, or an acid addition salt thereof (e.g., from 0.5 to 5 mg, 4 to 10 mg, 6 to 15 mg, 8 to 12 mg, 10 to 15 mg. 15 to 25 mg, or 20 to 30 mg of dihydroergocryptine, or an acid addition salt thereof). For example, each unit dosage form can contain 1±0.5 mg, 3±1 mg, 4±1 mg, 5±1 mg, 8±2 mg, 10±3 mg, 12±3 mg. 15±3 mg, 22±4 mg, 27±4 mg, or 30±5 mg of dihydroergocryptine, or an acid addition salt thereof.

In an embodiment of any of the above pharmaceutical compositions, the pharmaceutical composition is in a unit dosage form including from 0.1 to 100 mg or 0.05 to 10 mg of lisuride, or an acid addition salt thereof (e.g., from 0.05 to 0.5 mg, 0.4 to 1 mg, 0.8 to 1.5 mg, 1 to 2 mg, 1.5 to 3 mg, 2.5 to 5 mg, or 5 to 10 mg of lisuride, or an acid addition salt thereof). For example, each unit dosage form can contain 0.1±0.05 mg, 0.3±0.1 mg, 0.4±0.1 mg, 0.5±0.1 mg, 1±0.5 mg, 2±1 mg, 3±1 mg, 5±2 mg, 7±2 mg, 9±2 mg, or 10±2 mg of lisuride, or an acid addition salt thereof.

In an embodiment of any of the above pharmaceutical compositions, the pharmaceutical composition is in a unit dosage form including from 0.1 to 100 mg or 0.5 to 75 mg of piribedil, or an acid addition salt thereof (e.g., from 0.5 to 5 mg, 4 to 10 mg, 6 to 15 mg, 8 to $1^2$ mg, 10 to 15 mg, 15 to 25 mg, 20 to 30 mg, 35 to 45 mg, 40 to 50 mg, or 50 to 75 mg of piribedil, or an acid addition salt thereof). For example, each unit dosage form can contain 1±0.5 mg, 3±1 mg, 4±1 mg, 5±1 mg, 8±2 mg, 10±3 mg, 12±3 mg, 15±3 mg, 22±4 mg, 27±4 mg, 30±5 mg, 40±10 mg, 50±10 mg, or 75±20 mg of piribedil, or an acid addition salt thereof.

In an embodiment of any of the above pharmaceutical compositions, the pharmaceutical composition is in a unit dosage form including from 0.1 to 100 mg or 0.05 to 10 mg of pergolide, or an acid addition salt thereof (e.g., from 0.05 to 0.5 mg, 0.4 to 1 mg, 0.8 to 1.5 mg, 1 to 2 mg, 1.5 to 3 mg, 2.5 to 5 mg, or 5 to 10 mg of pergolide, or an acid addition salt thereof). For example, each unit dosage form can contain 0.1±0.05 mg, 0.3±0.1 mg, 0.4±0.1 mg, 0.5±0.1 mg, 1±0.5 mg, 2±1 mg, 3±1 mg, 5±2 mg, 7±2 mg, 9±2 mg, or 10±2 mg of pergolide, or an acid addition salt thereof.

In an embodiment of any of the above pharmaceutical compositions, the pharmaceutical composition is in a unit dosage form including from 0.1 to 100 mg or 0.1 to 20 mg of pramipexole, or an acid addition salt thereof (e.g., from 0.1 to 0.5 mg, 0.2 to 2 mg, 0.5 to 3 mg, 1 to 4 mg, 3 to 7 mg, 6 to 11 mg, 9 to 15 mg, 13 to 18 mg, or 16 to 20 mg of pramipexole, or an acid addition salt thereof). For example, each unit dosage form can contain 0.2±0.1 mg, 0.5±0.25 mg, 1±0.5 mg, 2±0.5 mg, 3±1 mg, 4±1.5 mg, 6±2 mg, 10±3 mg, 14±3 mg, 18±3 mg, or 20±5 mg of pramipexole, or an acid addition salt thereof.

In an embodiment of any of the above pharmaceutical compositions, the pharmaceutical composition is in a unit dosage form including from 0.1 to 100 mg or 0.1 to 20 mg of rotigotine, or an acid addition salt thereof (e.g., from 0.1 to 0.5 mg, 0.2 to 2 mg, 0.5 to 3 mg, 1 to 4 mg, 3 to 7 mg, 6 to 11 mg, 9 to 15 mg, 13 to 18 mg, or 16 to 20 mg of rotigotine, or an acid addition salt thereof). For example, each unit dosage form can contain 0.2±0.1 mg, 0.5±0.25 mg, 1±0.5 mg, 2±0.5 mg, 3±1 mg, 4±1.5 mg, 6±2 mg, 10±3 mg, 14±3 mg, 18±3 mg, or 20±5 mg of rotigotine, or an acid addition salt thereof.

In a particular embodiment of any of the above pharmaceutical compositions, the unit dosage form when administered sublingually to a subject is non-irritating.

In still another embodiment of any of the above pharmaceutical compositions wherein the dopamine agonist is selected from apomorphine, an apomorphine prodrug, or a salt thereof, following sublingual administration to a subject the unit dosage form produces an average circulating apomorphine concentration of at least 3 ng/mL within a period of from 5 to 15 minutes following the administration. For example, the unit dosage form can produce an average circulating concentration of from 3 to 6 ng/mL within 7 to 10 minutes, from 5 to 10 ng/mL within 5 to 10 minutes, from 7 to 12 ng/mL within 5 to 10 minutes, from 10 to 16 ng/mL within 5 to 10 minutes, from 3 to 6 ng/mL within 7 to 15 minutes, from 5 to 10 ng/mL within 7 to 15 minutes, from 7 to 12 ng/mL within 7 to 15 minutes, from 10 to 16 ng/mL within 7 to 15 minutes, from 3 to 6 ng/mL within 15 to 20 minutes, from 5 to 10 ng/mL within 15 to 20 minutes, from 7 to 12 ng/mL within 15 to 20 minutes, or from 10 to 16 ng/mL within 15 to 20 minutes following the administration.

In another embodiment of any of the above pharmaceutical compositions, the unit dosage form when placed in 1 mL of unbuffered water at pH 7 results in a solution having a pH of between 2.5 and 8.0, preferably between 4.5 and 6.5, (e.g., a pH of between 2.5 and 4.5, 3.0 and 6.5, 3.5 and 7.5, 4.5 and 8.0, or 6.5 and 8.0). For example, the films of the invention can include a neutralizing layer that controls the pH of the dissolved pharmaceutical composition and produces a predetermined pH value upon dissolution.

In another embodiment of any of the above pharmaceutical compositions, the unit dosage form has a sublingual bioavailability of greater than of greater than 40% (e.g., a sublingual bioavailability of from 40 to 70%, 45 to 85%, 55 to 95%, 65 to 100%. 70 to 100%. 70 to 99%. 75 to 100%, 75 to 99%, or 80 to 99%).

The invention further features a method of treating movement disorders, such as Parkinson's disease, restless leg syndrome, or tremor, in a subject by sublingually administering a pharmaceutical composition of the invention to the subject in an amount effective to treat the subject.

The invention also features a method for alleviating dyskinesia in a subject afflicted with Parkinson's disease by sublingually administering a pharmaceutical composition of the invention to the subject in an amount effective to alleviate the dyskinesia.

The invention also features a method for alleviating akinesia in a subject afflicted with Parkinson's disease by sublingually administering a pharmaceutical composition of the invention to the subject in an amount effective to alleviate the akinesia.

The invention features a method of treating sexual dysfunction in a subject by sublingually administering a pharmaceutical composition of the invention to the subject in an amount effective to treat the subject.

The invention also features a method of treating a depressive disorder in a subject by sublingually administering a pharmaceutical composition of the invention to the subject in an amount effective to treat the subject.

In one embodiment of any of the above methods, the method further includes administration of an effective amount of an anti-emetic agent (e.g., nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride, or diphenidol hydrochloride).

The invention feature a method of preparing a bilayer film having a first layer and a second layer, the method including:

(i) forming a first viscous solution by mixing an aqueous solution including a volatile organic solvent with (a) from 30 to 75% (w/w) (e.g., 30±5%. 35±5%, 40±5%. 45±5%. 50±5%, 55±5%. 60±5%. 65±5%, 70±5%, or 75±5% (w/w)) dopamine agonist, or an acid addition salt thereof (e.g., apomorphine, an apomorphine prodrug, bromocriptine, cabergoline, dihydroergocryptine, lisuride, piribedil, pergolide, pramipexole, rotigotine, ropinirol, or an acid addition salt thereof); (b) from 0.5 to 16% (w/w) (e.g., 0.5 to 10%, 0.5±0.1%, 1±0.5%, 2±0.75%, 3±1%. 5±1%. 6±2%, 7±3%. 8±3%. 9±3%. 12±3%, or 16±3% (w/w)) of a low molecular weight polymer having a weight average molecular weight of from 5 KDa to 50 KDa (e.g., 5±3, 8±3%. 10±3, 15±5, 18±5, 22±6, 28±6, 34±8, 44±8, or 50±10 KDa) selected from hydroxypropyl cellulose, hydroxypropyl methyl cellulose, hydroxyethyl cellulose, carboxymethyl cellulose, and methyl cellulose: (c) from 4 to 35% (w/w) (e.g., 4 to 20%, 4±2%, 5±2.5%. 7.5±3%. 10±3.5%, 14±5%, 18±5%. 20±6%, 25±6%, 30±6%, or 35±6% (w/w)) of a high molecular weight polymer having a weight average molecular weight of greater than 60 KDa (e.g., 60 KDa to 500 KDa, 60 KDa to 1,000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose: (d) from 3 to 18% (w/w) (e.g., 3 to 12%, 3±1%, 5±2%, 7.5±2.5%, 10±3%, 12±3%. 15±3%, or 18±3% (w/w)) of a plasticizing agent; and (e) from 1 to 50% (w/w) (e.g., 1±0.75%, 2±1.5%, 3±0.5%, 5±2%, 7.5±2.5%, 10±2%, 14±3%. 18±4%, 22±5%, 25±5%. 30±5%, 35±5%, 40±5%. 45±5%, or 50±5% (w/w)) hydrolyzed starch;

(ii) casting the first viscous solution onto an inert support, and drying the solution to form a first film layer;

(iii) forming a second viscous solution by mixing an aqueous solution including a volatile organic solvent with (a) from 15 to 50% (w/w) (e.g., 15±5%. 20±5%, 25±5%. 30±5%. 35±5%, 40±5%. 45±5%, or 50±5% (w/w)) of a high molecular weight polymer having a weight average molecular weight of greater than 60 KDa (e.g., 60 KDa to 500 KDa, 60 KDa to 1,000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose; (b) from 6 to 65% (w/w) (e.g., 10 to 50%. 6±2%. 8±2%. 10±2%, 14±3%, 18±4%. 22±5%, 25±5%, 30±5%, 35±5%. 40±5%, 45±5%, 50±5%. 55±5%, 60±5%, or 65±5% (w/w)) pH neutralizing agent; (c) from 3 to 18% (w/w) (e.g., 3 to 12%, 3±1%, 5±2%, 7.5±2.5%, 10±3%. 12±3%, 15±3%, or 18±3% (w/w)) of a plasticizing agent; and (d) from 1 to 50% (w/w) (e.g., 1±0.75%. 2±1.5%. 3±0.5%, 5±2%, 7.5±2.5%, 10±2%, 14±3%. 18±4%, 22±5%, 25±5%. 30±5%, 35±5%, 40±5%. 45±5%, or 50±5% (w/w)) hydrolyzed starch;

(iv) casting the second viscous solution onto an inert support, and drying the solution to form a second film layer;

(v) contacting faces of the first film layer and the second film layer with a volatile organic solvent, pressing the faces together such that volatile organic solvent is sandwiched between the first film layer and the second film layer, and drying the layers to form a bilayer film.

The invention feature a method of preparing a bilayer film having a first layer and a second layer, the method including:

(i) forming a first viscous solution by mixing an aqueous solution including a volatile organic solvent with (a) from 30 to 75% (w/w) (e.g., 30±5%, 35±5%. 40±5%, 45±5%, 50±5%. 55±5%, 60±5%, 65±5%. 70±5%, or 75±5% (w/w)) apomorphine, an apomorphine prodrug, or an acid addition salt thereof; (b) from 0.5 to 16% (w/w) (e.g., 0.5 to 10%. 0.5±0.1%. 1±0.5%. 2±0.75%. 3±1%, 5±1%, 6±2%, 7±3%, 8±3%. 9±3%. 12±3%, or 16±3% (w/w)) of a low molecular weight polymer having a weight average molecular weight of from 5 KDa to 50 KDa (e.g., 5±3, 8±3%. 10±3, 15±5, 18±5, 22±6, 28±6, 34±8, 44±8, or 50±10 KDa) selected from hydroxypropyl cellulose, hydroxypropyl methyl cellulose, hydroxyethyl cellulose, carboxymethyl cellulose, and methyl cellulose; (c) from 4 to 35% (w/w) (e.g., 4 to 20%, 4±2%, 5±2.5%, 7.5±3%, 10±3.5%, 14±5%. 18±5%, 20±6%, 25±6%. 30±6%, or 35±6% (w/w)) of a high molecular weight polymer having a weight average molecular weight of greater than 60 KDa (e.g., 60 KDa to 500 KDa, 60 KDa to 1,000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose: (d) from 3 to 18% (w/w) (e.g., 3 to 12%.

3±1%, 5±2%, 7.5±2.5%, 10±3%, 12±3%, 15±3%, or 18±3% (w/w)) of a plasticizing agent; and (e) from 1 to 50% (w/w) (e.g., 1±0.75%, 2±1.5%, 3±0.5%, 5±2%, 7.5±2.5%, 10±2%, 14±3%, 18±4%, 22±5%, 25±5%, 30±5%, 35±5%, 40±5%, 45±5%, or 50 t 5% (w/w)) hydrolyzed starch;

(ii) casting the first viscous solution onto an inert support, and drying the solution to form a first film layer;

(iii) forming a second viscous solution by mixing an aqueous solution including a volatile organic solvent with (a) from 15 to 50% (w/w) (e.g., 15±5%, 20±5%, 25±5%, 30±5%, 35±5%, 40±5%, 45±5%, or 50±5% (w/w)) of a high molecular weight polymer having a weight average molecular weight of greater than 60 KDa (e.g., 60 KDa to 500 KDa, 60 KDa to 1.000 KDa, 80 KDa to 120 KDa, 100 KDa to 300 KDa, 220 KDa to 500 KDa, or 400 KDa to 800 KDa) selected from hydroxypropyl cellulose, hydroxypropyl methyl cellulose, hydroxyethyl cellulose, carboxymethyl cellulose, and methyl cellulose; (b) from 6 to 65% (w/w) (e.g., 10 to 50%, 6±2%, 8±2%, 10±2%, 14±3%, 18±4%, 22±5%, 25±5%, 30±5%, 35±5%, 40±5%, 45±5%, 50±5%, 55±5%, 60±5%, or 65±5% (w/w)) pH neutralizing agent; (c) from 3 to 18% (w/w) (e.g., 3 to 12%, 3±1%, 5±2%, 7.5±2.5%, 10±3%, 12±3%, 15±3%, or 18±3% (w/w)) of a plasticizing agent; and (d) from 1 to 50% (w/w) (e.g., 1±0.75%, 2±1.5%, 3±0.5%, 5±2%, 7.5±2.5%, 10±2%, 14±3%, 18±4%, 22±5%, 25±5%, 30±5%, 35±5%, 40±5%, 45±5%, or 50±5% (w/w)) hydrolyzed starch;

(iv) casting the second viscous solution onto an inert support, and drying the solution to form a second film layer;

(v) contacting faces of the first film layer and the second film layer with a volatile organic solvent, pressing the faces together such that volatile organic solvent is sandwiched between the first film layer and the second film layer, and drying the layers to form a bilayer film.

The volatile organic solvent (e.g., an organic solvent having a boiling point of between 20° C. and 80° C.) can include acetone, ethanol, isopropyl alcohol, diethyl ether, butanol, propanol, ethyl acetate, or combinations thereof.

In certain embodiments of the method, the plasticizing agent is a polyol (e.g., sorbitol, mannitol, maltitol, xylitol, glycerol, propylene glycol, or polyethylene glycol), oleic acid, or triacetin. In particular embodiments of the method, the hydrolyzed starch is a dextrin or a maltodextrin. The method can be used to produce any bilayer film of the invention described herein.

In still other embodiments of the method, the dopamine agonist is apomorphine or apomorphine prodrug. For example, the apomorphine or apomorphine prodrug can be an acid addition salt of apomorphine, such as apomorphine hydrochloride. The apomorphine hydrochloride can be milled to produce material having an effective particle size of from 0.5 μm to 50 μm (e.g., an effective particle size of from 1 μm to 10 μm, 1 μm to 9 μm, from 1 μm to 8 μm, from 1 μm to 7 μm, from 1 μm to 6 μm, from 1 μm to 5 μm, from 2 μm to 10 μm, from 3 μm to 10 μm, from 4 μm to 10 μm, from 2 μm to 7 μm, 2 μm to 6 μm, 0.5 μm to 25 μm, 0.5 μm to 20 μm, or from 5 μm to 12 μm) prior to the addition of the apomorphine hydrochloride to the mixture of step (i).

In an embodiment of any of the above methods and compositions in which the dopamine agonist includes apomorphine or apomorphine prodrug, the apomorphine, apomorphine prodrug, or salt thereof is a racemic mixture of R and S isomers, or enriched in R isomer (i.e., the ratio of R to S isomer for all of the apomorphine in the composition, or all the apomorphine being administered, is from 5:1 to 1.000:1, from 10:1 to 10,000:1, or from 100:1 to 100.000:1, or over all apomorphine isomers in the composition is at least 98% R isomer, 99% R isomer, 99.5% R isomer, 99.9% R isomer, or is free of any observable amount of S isomer.

The term "administration" or "administering" refers to a method of giving a sublingual dosage of dopamine agonist to a patient.

As used herein, the term "apomorphine particle" refers to microparticles or nanoparticles containing apomorphine, an apomorphine prodrug, or salts thereof.

As used herein, the term "dopamine agonist particle" refers to microparticles or nanoparticles containing a dopamine agonist (e.g., apomorphine, an apomorphine prodrug, bromocriptine, cabergoline, dihydroergocryptine, lisuride, piribedil, pergolide, pramipexole, rotigotine, ropinirol, or an acid addition salt thereof).

As used herein, the term "average circulating concentration" refers to the average plasma concentration of apomorphine at time t observed for a group of subjects following sublingual administration of a particular unit dosage form of the invention. For example, among 20 subjects the average circulating concentration concentration of apomorphine 10 minutes following sublingual administration of the unit dosage form can be at least 3 ng/mL, 5 ng/mL, 7 ng/mL, 9 ng/mL, 11 ng/mL, 13 ng/mL, or 15 ng/mL, depending upon the amount of apomorphine in the unit dosage.

By "depressive disorder" is meant any psychological or psychiatric disorder associated with symptoms of depressed mood. Treatable depressive disorders may be characterized by an inhibition or reduction of dopaminergic function in the nucleus accumbens, e.g., major depression, dysthymia, bipolar disorder (manic depression), and post-traumatic stress disorder.

As used herein, the terms "effective particle size" and "particle size" are used interchangeably and refer to a mixture of particles having a distribution in which 50% of the particles are below and 50% of the particles are above a defined measurement. The "effective particle size" refers to the volume-weighted median diameter as measured by a laser/light scattering method or equivalent, wherein 50% of the particles, by volume, have a smaller diameter, while 50% by volume have a larger diameter. The effective particle size can be measured by conventional particle size measuring techniques well known to those skilled in the art. Such techniques include, for example, sedimentation field flow fractionation, photon correlation spectroscopy, light scattering (e.g., with a Microtrac UPA 150), laser diffraction, and disc centrifugation.

As used herein, the term "apomorphine prodrug" refers to apomorphine esters and glycosides of formula (I):

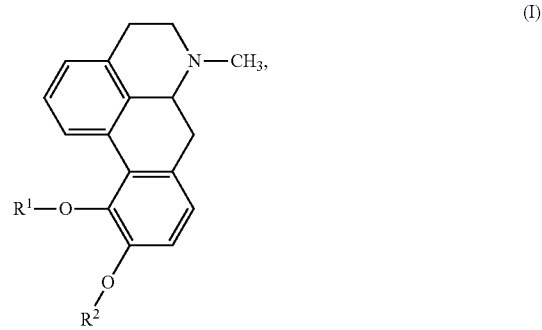

(I)

and acid addition salts thereof. In formula I, each of $R^1$ and $R^2$ is, independently, H, $C(O)—R_3$, $C(O)—O—R_3$, or a glycoside of a monosaccharide or oligosaccharide; or $R^1$ and $R^2$ combine with the oxygen atoms to which they are bound to form a cyclic acetal, cyclic ketal, a cyclic carbonate (i.e., —C(O)—O—C(O)—), or an orthoester glycoside; and $R_3$ is a cyclic, straight chained, or branched hydrocarbon of 1 to 12 carbon atoms, which is optionally saturated (i.e., a $C_{1-12}$ alkyl), includes one or more carbon-carbon double bonds (i.e., a $C_{2-12}$ alkenyl), and/or includes one or more carbon-carbon triple bonds (i.e., a $C_{2-12}$ alkynyl). For example, the apomorphine glycosides can be glycosides of straight or branched chain glycosidic moiety containing 1-20 glycosidic units. Apomorphine glycosides and orthoester glycosides can be synthesized as described in PCT Publication No. WO/2003/080074. Apomorphine esters, cyclic acetals, and cyclic ketals can be synthesized using methods analogous to those described in U.S. Pat. No. 4,687,773, Borgman et al., J. Med. Chem., 19:717 (1976), and PCT Publication No. WO/2005/099702. The above patent publications are incorporated herein by reference. Carbonate esters of apomorphine can be prepared as described in Atkinson et al., J. Pharma. Sci. 65:1685 (1976), and in Campbell et al., Neuropharmacology 21:953 (1982). Apomorphine prodrugs which can be used in the unit dosage forms of the invention include, without limitation, O,O'-diacetylapomorphine. O,O'-dipropionylapomorphine. O,O'-diisobutyrylapomorphine. O,O'-dipivaloylapomorphine. O,O'-dibenzoylapomorphine, apomorphine carbonate, apomorphine diethylcarbonate, apomorphine methylene acetal, apomorphine ethyl acetal, apomorphine dimethyl acetal, and acid addition salts thereof.

As used herein, the term "non-irritating" refers to pharmaceutical compositions of the invention which, using the irritation test described in Example 7, either: (i) following administration to un-abraded cheek exhibit irritation that is equal to or less than that observed for an unbuffered acidic control film that produces a local pH of less than 3 following administration to, and dissolution in, a cheek pouch; and/or (ii) following administration to abraded cheek exhibit a healing time that is equal to or less than that observed for an unbuffered acidic control film that produces a local pH of less than 3 following administration to, and dissolution in, a cheek pouch.

As used herein, "pH neutralizing agent" refers to any basic component present in the unit dosage forms of the invention. The pH neutralizing agents which can be used in the unit dosage forms of the invention include organic bases (e.g., amines), inorganic bases (e.g., oxides, hydroxides, carbonates, or phosphates), and mixtures thereof. The pH neutralizing agent is typically present in an amount sufficient to produce a solution having a pH of between 2.5 and 8.0, preferably between 4.5 and 6.5, when the unit dosage form is placed in 1 mL of unbuffered water at pH 7.

As used herein, "sexual dysfunction" refers to disorders of orgasm, response timing, ejaculation, nociception, congestive arousal and erection, vasculogenic impairment, or desire. In males, the form of sexual dysfunction is typically erectile dysfunction, the inability to achieve and sustain an erection sufficient for intercourse. Females also can have sexual dysfunctions of arousal and orgasm that increase with age and are associated with the presence of vascular risk factors and onset of menopause.

Some of the vascular and muscular mechanisms that contribute to penile erection in the male are believed to involve similar vasculogenic factors in female genital responses. Female sexual dysfunction includes a failure to attain or maintain vaginal lubrication-swelling responses of sexual excitement until completion of the sexual activity.

As used herein, the term "sublingual bioavailability" refers to the average sublingual bioavailability of dopamine agonist formulated as described herein and administered sublingually in a study of 5 or more rabbits in comparison to 100% bioavailability for subcutaneously administered dopamine agonist. Sublingual bioavailability can be determined from a pharmacokinetic study as described in Example 2.

As used herein, the term "$T_{max}$" refers to the average time, following sublingual administration of a dopamine agonist formulated as described, to the maximum circulating concentration in a study of 5 or more rabbits. $T_{max}$ can be determined from a pharmacokinetic study as described in Example 2.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a subject either for therapeutic or prophylactic purposes.

Other features and advantages of the invention will be apparent from the following Detailed Description, the Drawings, and the Claims.

DETAILED DESCRIPTION

Figure 1:
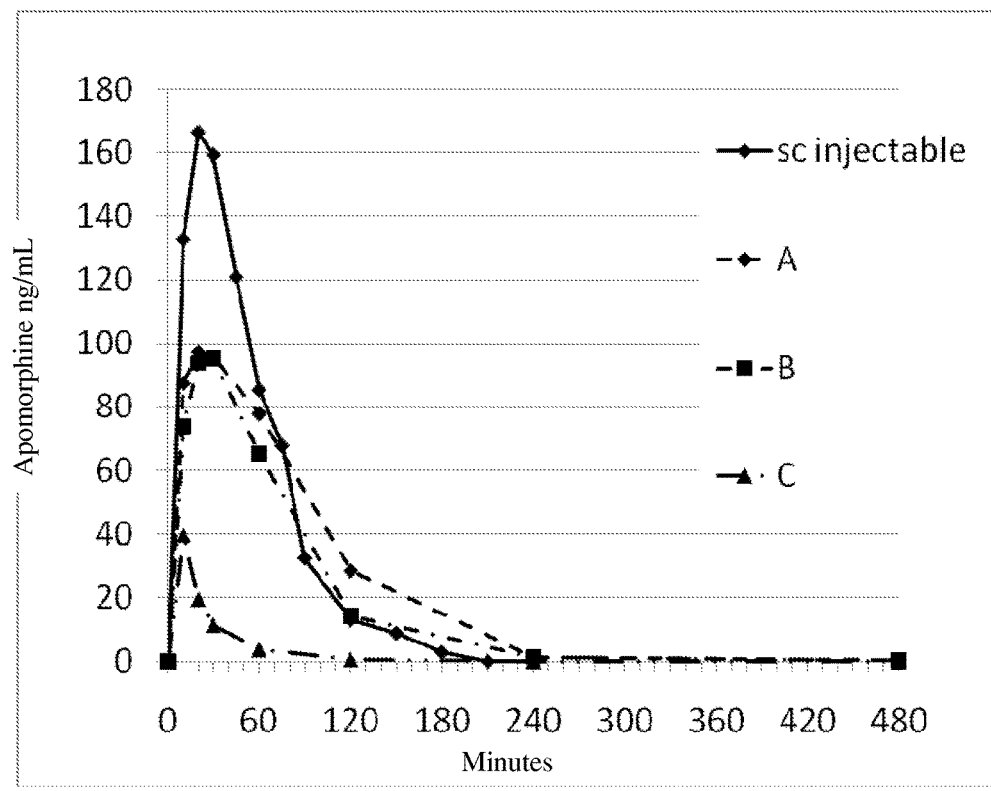
FIG. 1 is a graph depicting the pharmacokinetic profile for films A, B, and C in comparison to subcutaneously administered apomorphine (see Examples 1 and 2).
Figure 2:
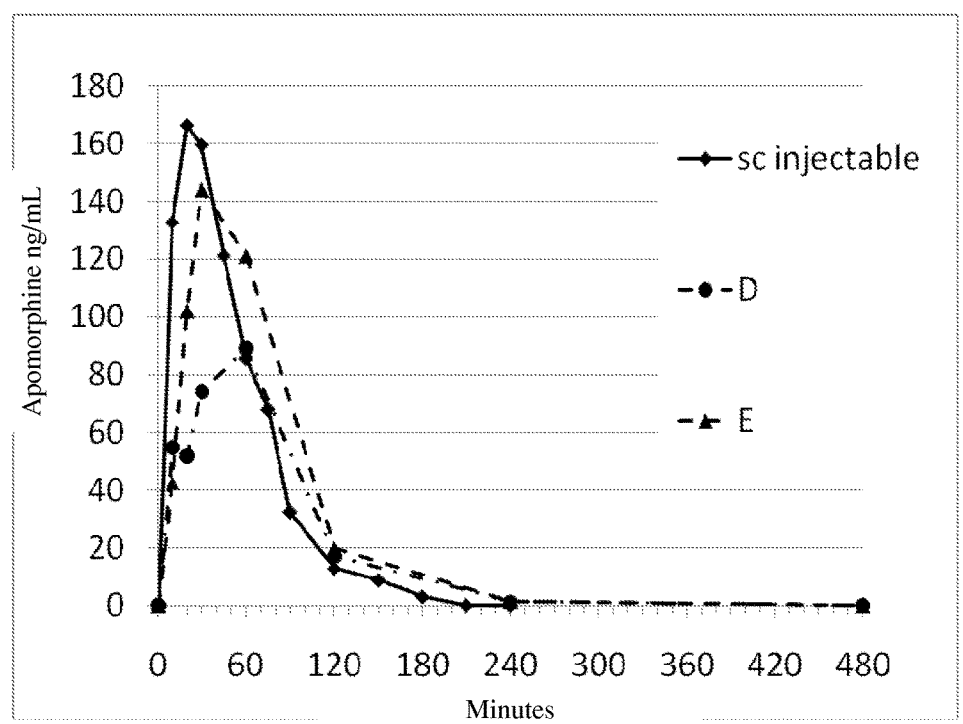
FIG. 2 is a graph depicting the pharmacokinetic profile for films D and E in comparison to subcutaneously administered apomorphine (see Examples 1 and 2).
Figure 3:
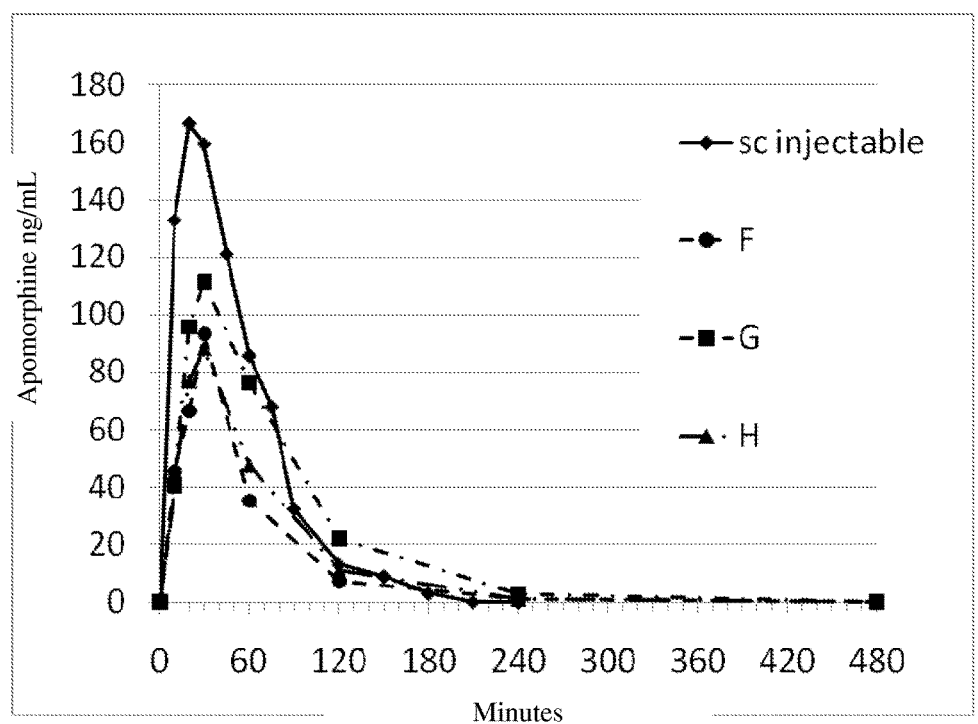
FIG. 3 is a graph depicting the pharmacokinetic profile for films F, G, and H in comparison to subcutaneously administered apomorphine (see Examples 1 and 2).
Figure 4:
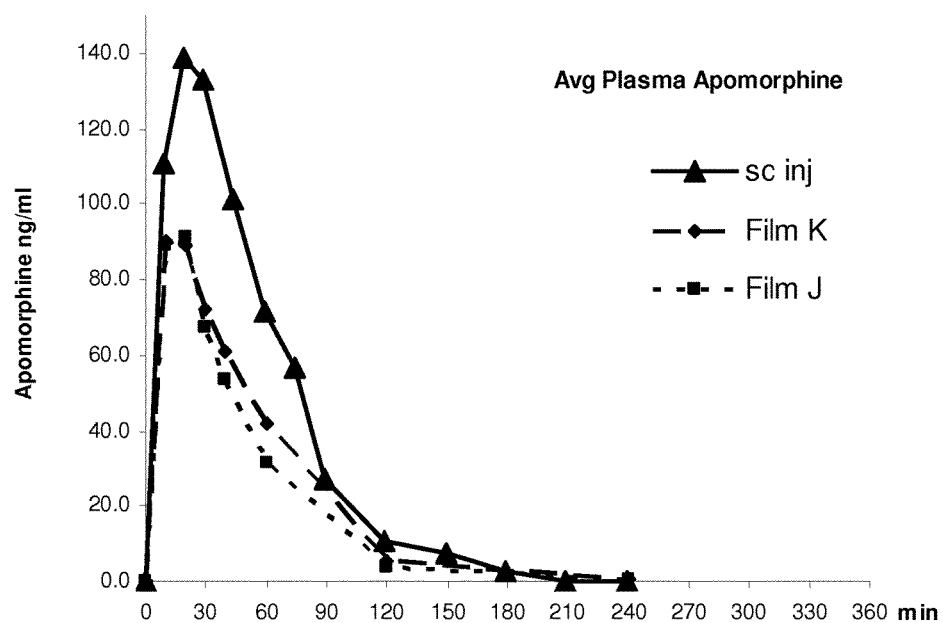
FIG. 4 is a graph depicting the pharmacokinetic profile for films J and K in comparison to subcutaneously administered apomorphine (see Examples 1 and 2).

The invention features sublingual formulations of dopamine agonists. The formulations can be useful for the treatment of Parkinson's disease, restless leg syndrome, tremors (among other movement disorders), sexual dysfunction, and depressive disorders therewith. The films can be a single layer or a bilayer (e.g., a unit dosage form having a first layer including an acid addition salt of apomorphine, or an apomorphine prodrug, and a second layer including a pH neutralizing agent).

Fluctuations in motor disability and dyskinesias are a significant problem in the long-term treatment of Parkinson's disease. In the later stages of Parkinson's disease, many patients develop severe "off" episodes where, despite continuing to take their medication, they experience periods when they lose the ability to move (e.g., the patients develop bradykinesia (slowed movement) or akinesia (inability to move)). These "off" episodes typically occur 3 to 4 times per day.

Apomorphine has a rapid onset of action which is ideal for use as a rescue therapy for intractable "off" periods in Parkinson's disease. Other dopamine agonists can also be useful.

Using the sublingual formulations of the invention, a subject suffering from the effects of middle stage or late stage Parkinson's disease may be able to recognize the onset of their "off" symptoms and be capable of administering a sublingual dose of a formulation of the invention to alleviate the dyskinesia associated with such "off" episodes. The sublingual formulations are easy for a subject with compromised motor skills to administer and can relieve a Parkinson's patient from the need for a caregiver, who might otherwise be needed to administer an injectable dosage form of apomorphine at the onset of an "off" episode.

The sublingual formulations of the invention can increase the bioavailability of the dopamine agonist, prolong the stability, in certain cases, of the dopamine agonist, and/or improve the safety and efficacy of the dopamine agonist therapy. The formulations can produce a rapid uptake of the dopamine agonist into the subject, allowing dyskinesia episodes to be self-treated. Furthermore, the convenience with which these sublingual formulations can be self administered provides a significant advantage to severely ill patients, such as those with middle stage or late stage Parkinson's disease.

The pharmaceutical compositions of the invention can provide a rapid-dissolving, rapid absorption solid oral dosage form that includes (i) an acid salt form of a dopamine agonist and (ii) a pH-modifying agent. Typically, the acid addition salt has high water solubility, which assists in achieving fast dissolution, a pre-requisite to fast absorption. Passive transcellular absorption is the primary route of absorption for dopamine agonists in the sublingual cavity. Passive absorption occurs by partition of the neutral, free-base or unionized form of the dopamine agonist into the tissues and through cellular membranes and is therefore partially determined by the 2 key factors: (i) the abundance of the neutral dopamine agonist species which is driven by an equilibrium of the ionized form (salt form) and the non-ionized form which is a function of the local pH and the pKa of the dopamine agonist: and (ii) the lipophilicity of the neutral dopamine agonist species. The inclusion of the pH-modifying agent helps to maintain a pH and favor deprotonation of the ionized form (salt form), thus, increasing the fraction of non-ionized species and increasing the rate of absorption.

Another benefit of the formulations of the invention is that they can be non-irritating at the site of administration. Irritation during sublingual or nasal delivery of a dopamine agonist is believed to arise in some instances because of absorption of the neutral form of the dopamine agonist in the absence of a pH-modifier. Passive trans-cellular absorption of the neutral species from the natural equilibrium of ionized and non-ionized species causes a displacement of the same equilibrium to replenish the solution concentration of the neural dopamine agonist species. In theory, such a displacement could lead to depletion of the agonist from solution, resulting in the release of the acid and a reduction in the local pH. The lower pH in turn can cause local irritation, especially in the case of repeated dosing, chronic administration.

Additional details of how to make and use the sublingual formulations of the invention are provided below and in the Examples.

Dopamine Agonists

Dopamine agonists which can be used in the compositions and methods of the invention include, without limitation, ergot and non-ergot dopamine agonists, such apomorphine, bromocriptine, cabergoline, dihydroergocryptine, lisuride, piribedil, pergolide, pramipexole, rotigotine, ropinirol, and acid addition salts thereof. The dopamine agonists can be formulated as described in the Examples.

Monolayer and Bilayer Films

The films of the invention are not dissimilar to the films used, for example, to make the Listerine® PocketPak® mouth fresheners.

The films can include one layer, two layers, or more. If in two layers, the one adapted to adhere to mucosal tissue may be referred to as the "adhesive layer." With two layers, the outer layer can be less adhesive or non-adhesive, and can provide protection against mechanical agitation, such as agitation by a user's tongue. The components of the outer layer might be, of themselves, less dissolvable than the components of an adhesive layer. However, in the aggregate, the film shall dissolve in that it will transition to fully dissolved parts or parts that will be carried away by normal cleaning processes at the mucosal tissue in question. In forming two layers, diffusion or the forming process itself may provide a gradient in component amounts in the transition between the two layers. The two layers can be utilized to separate components (e.g., a dopamine agonist-containing acidic layer and a buffered pH neutralizing layer), which together can enhance absorption, reduce irritation, and/or improve stability of the dopamine agonist, but which may otherwise be incompatible in certain formulations requiring long term stability (i.e., shelf life). The two component layers of the bilayer can be laminated together using combinations of water, heat, solvent and aqueous, organic or mixed aqueous-organic solutions containing any one or combination of polymer(s), low molecular weight sugar(s), stabilizer(s), flavor(s), sweetener(s), permeation enhancer(s) or other desirable agent.

Alternatively, the unit dosage form of the invention can be a monolayer film that is an dopamine agonist-containing acidic layer which is coated with or impregnated with a particulate base. The particulate base can be incorporated into the monolayer film using the methods described in PCT Publication No. WO/2009/052421. U.S. Patent Publication No. 20060210610, each of which is incorporated herein by reference. The film of the invention can include an effervescent particulate (i.e., a particulate carbonate base) or disintegrant (e.g., materials that favor disintegration or fast dissolution by virtue of their solubility in water, such as hydrolyzed starches, sugars, and glycerin, which may play a dual role as a plasticizer and disintegrant). Such effervescent films can be prepared as described in U.S. Patent Publication No. 20010006677, incorporated herein by reference.

The polymers used in the films of the invention can be polymers that affect the rate of hydration or mucosal adhesion properties of an adhesive layer. Such polymers can be, for example, carboxymethylcellulose, hydroxypropyl cellulose, hydroxypropyl methyl cellulose (HPMC, such as Pharmacoat 606™. Shin-Etsu Chemical Company Ltd., Japan), hydroxyethyl cellulose (HEC, commercially available from Hercules Incorporated, Aqualon Division under the tradename NATROSOL™), and methyl cellulose, optionally in a mixture with other polymers, such as polyoxyethylene/polyoxypropylene polymers, copolymers or block copolymers, polyvinylpyrrolidone polymers or derivatives, and/or gums. The average molecular weight of the polymer can be selected based on the swelling and dissolution profile sought.

The films of the invention can include blends of one or more low molecular weight polymers (e.g., those from about 5 KDa to about 50 KDa) and high molecular weight polymers (e.g., those from about 60 KDa to about 500 KDa) in order to achieve desirable properties of dissolution and mechanical strength. For example, a combination of hydroxypropyl cellulose (e.g., Klucel, grade JF, Hercules Inc., Aqualon Division) and hydroxypropyl methylcellulose (e.g., Methocel, grades E5, E50. E4M, and SG A16M by Dow Chemical) can be used. These water soluble cellulose derivative polymers have molecular weights of about 140.000; 30.000; 90.000; 400,000; and greater than about 100,000 daltons, respectively. The molecular weights of the water soluble polymers can be determined as described in Keary, Carbohydrate Polymers 45:293 (2001), which is incorporated herein by reference.

Mixtures of less soluble and/or less swellable polymers with more soluble or more swellable polymers can help transition the film to a sufficiently dissolved form. For example, the film can include carbamer, polyethylene oxide, ethylcellulose, titanium oxide and colorant (such as F, D and C blue lake colorant). Often the film is formed using a pharmaceutically appropriate solvent such as ethanol, water, mixtures, or the like. Such solvents are typically largely evaporated away prior to use. Optionally, the films comprise a blend of more than one polymers or more than one molecular weight of a given set of polymers in order to control the rate of hydration, physical properties and mechanical properties.

The film of the invention can, optionally, be a multilaminate product including a monolayer or bilayer of the invention affixed to an additional slow-dissolving outer layer. Such a multilaminate film would be placed with this slow-dissolving layer away from the mucosal layer, such that it creates a barrier layer and provides for directional delivery of the dopamine agonist to the mucosa, increasing the rate of uptake.

Basic Layers

The multi-layered films of the invention can include a film formed from a basic polymer. Polyamines which can be used in the unit dosage forms of the invention include homo and copolymers of dimethylaminoethyl-acrylate, dimethylaminoethyl-methacrylate, dimethylaminopropyl-acrylate, dimethylaminpropyl-methacrylate, or other similar amino-functionalized acrylate, chitosan or partially hydrolyzed chitin in a substantially basic form, homo and co polymers of polyethyleimine, polylysine, polyvinylimidazole, or polyvinylamine. In certain embodiments the polyamine is Eudragit E100.

Other Components

Plasticizers, penetration enhancers, flavoring agents, preservatives, odorants, coloring agents, and the like can be included in the unit dosage forms of the invention.

Plasticizers will generally modify the feel, softness, flexibility (in an un-wetted state) of the unit dosage forms of the invention. Penetration enhancers may, in some cases, act as plasticizers. Examples of plasticizers include, without limitation, glycerol, propylene glycol, fatty acid esters, such as glyceryl oleate, polyalcohols, sorbitan esters, citric acid esters, polyethylene glycol (e.g., PEG 400), polyvinyl alcohol, polyvinyl methyl ether, triacetin; mannitol, xylitol, and sorbitol. The plasticizer can be present in any suitable range, including, for example about 0.5% to 30%. 10% to 20%, or 15% to 18% by weight of the dry film.

Permeation enhancers can be used to improve the permeability of the dopamine agonist at the mucosal membrane in the unit dosage forms of the invention. One or more permeation enhancers maybe used to modulate the rate of mucosal absorption of the dopamine agonist. Any effective permeation enhancers may be used including, for example, ionic surfactants, nonionic surfactants, bile salts, such as sodium cholate, sodium glycocholate, sodium glycodeoxycholate, taurodeoxycholate, sodium deoxycholate, sodium lithocholate chenocholate, chenodeoxycholate, ursocholate, ursodeoxy-cholate, hyodeoxycholate, dehydrocholate, glycochenocholate, taurochenocholate, and taurochenodeoxycholate; sodium dodecyl sulfate (SDS), dimethyl sulfoxide (DMSO), N-lauroyl sacrcosine, sorbitan monolaurate, stearyl methacrylate. N-dodecylazacycloheptan-2-one. N-dodecyl-2-pyrrolidinone. N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid. 2-pentyl-2-oxo-pyrrolidineacetic acid. 2-dodecyl-2-oxo-1-pyrrolidineacetic acid, 2-dodecyl-2-oxo-1-pyrrolidineacetic acid. 1-azacylioheptan-2-one-dodecylacetic acid, menthol, propylene glycol, glycerol monostearate, sorbitol monolaurate, glycerol dilaurate, tocopherol acetate, phosphatidyl choline, glycerol, polyethyleneglycol, monoglycerides, such as glycerol monostearate, glycerol monoloaurate, glycerol caprylate, diglycerides, triglycerides, and succinylated diglycerides and monoglycerides, such as glycerol succinyl caprylate lecithin, tween surfactants, sorbitan surfactants, sodium lauryl sulfate; salts, acids and other derivatives of saturated and unsaturated fatty acids, fatty alcohols, surfactants, bile salt analogs, derivatives of bile salts, or such synthetic permeation enhancers as described in U.S. Pat. No. 4,746,508, which is incorporated herein by reference.

A sweetener, flavoring agent and/or odorant can be added to the unit dosage forms of the invention to make them more palatable. At least one flavoring agent or odorant composition may be used. Any effective flavor or odor may be rendered. The flavoring agents may be natural, artificial, or a mixture thereof. The flavoring agent gives a flavor that is will help to reduce the undesirable taste of the active ingredient. In one embodiment, the flavoring agent may give the flavor of mint, menthol, honey lemon, orange, lemon lime, grape, cranberry, vanilla berry, bubble gum, or cherry. The flavoring agent can be natural or artificial sweetener, such as sucrose. Magnasweet™, sucralose, xylitol, sodium saccharin, cyclamate, aspartame, acesulfame, and salts thereof.

Apomorphine is susceptible to oxidative degradation. To minimize oxidative degradation it is desirable that the formulations of the invention contain one or more antioxidants. Antioxidants that can be used in the films of the invention can be selected from thiols (e.g., aurothioglucose, dihydrolipoic acid, propylthiouracil, thioredoxin, glutathione, cysteine, cystine, cystamine, thiodipropionic acid), sulphoximines (e.g., buthionine-sulphoximines, homo-cysteine-sulphoximine, buthionine-sulphones, and penta-, hexa- and heptathionine-sulphoximine), metal chelators (e.g. α-hydroxy-fatty acids, palmitic acid, phytic acid, lactoferrin, citric acid, lactic acid, and succinic acid, malic acid, humic acid, bile acid, bile extracts, bilirubin, biliverdin, EDTA. EGTA, and DTPA and salts thereof), sodium metabisulfite, sodium thiosulfate, vitamins and vitamin derivatives (e.g., vitamin E, vitamin C, ascorbyl palmitate, Mg ascorbyl phosphate, and ascorbyl acetate), phenols (e.g., butylhydroxytoluene, butylhydroxyanisole, ubiquinol, nordihydroguaiaretic acid, trihydroxybutyrophenone), benzoates (e.g., coniferyl benzoate), uric acid, mannose, propyl gallate, selenium (e.g., selenium-methionine), stilbenes (e.g., stilbene oxide and trans-stilbene oxide), and combinations thereof. The total amount of antioxidant included in the films can be from 0.001% to 3% by weight, preferably 0.01% to 1% by weight, in particular 0.05% to 0.5% by weight, based on the total weight of the formulation. Other dopamine agonists may also benefit from the inclusion of antioxidants in the formulations of the invention.

The films of the invention can include from 1 to 50% (ww) of one or more hydrolyzed starches. Various hydrolyzed starches may be utilized including maltrodextrins with a DE greater than 10 and dried glucose syrups which have a DE above 20. Suitable hydrolyzed starch products are commercially available from Grain Processing Corporation of Muscatine. Iowa under trademarks such as MALTRIN M200®, MALTRIN 180®, and MALTRIN 250®. MALTRIN M200® is a hydrolyzed starch product having a DE of 20, and MALTRIN 180® is a hydrolyzed starch product having a DE of 18. Dextrose equivalent (DE) is the relative sweetness of sugars, oligosaccharides, or blends compared to dextrose, both expressed as a percentage. For example, a maltodextrin with a DE of 10 would be 10% as sweet as dextrose (DE=100), while sucrose, with a DE of 120, would be 1.2 times as sweet as dextrose. For solutions made from starch, it is an estimate of the percentage reducing sugars present in the total starch product. The DE describes the degree of conversion of starch to dextrose: starch is close to 0, glucose/dextrose is 100 (percent), dextrins vary between 1 and 13, and maltodextrins vary between 3 and 20. The DE gives an indication of the average degree of polymerisation (DP) for starch sugars. The rule of thumb is $$DE \times DP = 120.$$

In certain embodiments, the various components (e.g., plasticizers, penetration enhancers, flavoring agents, preservatives, odorants, coloring agents, particulate base, and dopamine agonist particles) included in the unit dosage forms of the invention can be combined and incorporated into a first portion that is acidic and includes the dopamine agonist, or combined and incorporated into a second portion that includes a pH neutralizing component, or the components may be divided between the two portions. In some instances it may be desirable to minimize interaction between the acidic portion of the unit dosage form and the basic portion of the unit dosage form by including a barrier between the two. For example, a barrier can be included in the unit dosage forms of the invention as a third layer interposed between the acidic layer and the basic layer of a multilayer sublingual dosage form. Alternatively, the barrier can be a rapidly dissolving coating on the surface of a particulate component in the unit dosage form, such as a coated particulate base coated onto, or embedded within, an acidic portion of the unit dosage form. In still another approach, the barrier can be a rapidly dissolving coating on the surface of dopamine agonist particles in the unit dosage form, which further includes a basic portion. These approaches can be utilized to ensure that the dopamine agonist-containing acidic portion of the unit dosage form is not neutralized prior to the administration to a subject.

Dopamine Agonist Particles

The pharmaceutical formulations described herein can include dopamine agonist particles having an effective particle size of from about 1 micron to about 10 microns. The starting dopamine agonist composition can be predominantly crystalline, predominantly amorphous, or a mixture thereof, and can include unmodified dopamine agonist.

In an alternative approach, the pharmaceutical formulations described herein can include dopamine agonist particles having an effective particle size of less than about 1 micron (i.e., nanoparticulate formulations). The starting dopamine agonist composition can be predominantly crystalline, predominantly amorphous, or a mixture thereof, and can include unmodified dopamine agonist.

These dopamine agonist particles can be made by using any method known in the art for achieving the desired particle sizes. Useful methods include, for example, milling, homogenization, supercritical fluid fracture, or precipitation techniques. Exemplary methods are described in U.S. Pat. Nos. 4,540,602; 5,145,684; 5,518,187; 5,718,388; 5,862,999; 5,665,331; 5,662,883; 5,560,932; 5,543,133; 5,534,270; and U.S. Pat. Nos. 5,510,118; 5,470,583, each of which is specifically incorporated by reference.

Milling to Obtain Submicron Dopamine Agonist Particles

In one approach, the dopamine agonist, or a salt thereof, is milled in order to obtain micron or submicron particles. The milling process can be a dry process, e.g., a dry roller milling process, or a wet process. i.e., wet-grinding. A wet-grinding process is described in U.S. Pat. Nos. 4,540,602, 5,145,684, 6,976,647 and EPO 498,482, the disclosures of which are hereby incorporated by reference. Thus, the wet grinding process can be practiced in conjunction with a liquid dispersion medium and dispersing or wetting agents such as described in these publications. Useful liquid dispersion media include safflower oil, ethanol, n-butanol, hexane, or glycol, among other liquids selected from known organic pharmaceutical excipients (see U.S. Pat. Nos. 4,540,602 and 5,145,684), and can be present in an amount of 2.0-70%. 3-50%, or 5-25% by weight based on the total weight of the dopamine agonist in the formulation.

The grinding media for the particle size reduction step can be selected from rigid media, typically spherical in shape, though non-spherical grinding media could also be used. The grinding media preferably can have a mean particle size from 1 mm to about 500 microns. For fine grinding, the grinding media particles can have a mean particle size from about 0.05 to about 0.6 mm. Smaller size grinding media will result in smaller size dopamine agonist particles as compared to the same conditions using larger sized grinding media. In selecting material, grinding media with higher density, e.g., glass (2.6 g/cm$^3$), zirconium silicate (3.7 g/cm$^3$), and zirconium oxide (5.4 g/cm$^3$) and 95% zirconium oxide stabilized with yttrium, can be utilized for more efficient milling. Alternatively, polymeric grinding media can be used. Polymeric resins suitable for use herein are chemically and physically inert, substantially free of metals, solvent and monomers, and of sufficient hardness and friability to enable them to avoid being chipped or crushed during grinding. Suitable polymeric resins include, without limitation, crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly (tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, and silicone containing polymers such as polysiloxanes.

Grinding can take place in any suitable grinding mill. Suitable mills include an airjet mill, a roller mill, a ball mill, an attritor mill, a vibratory mill, a planetary mill, a sand mill and a bead mill. A high energy media mill is preferred when small particles are desired. The mill can contain a rotating shaft.

The preferred proportions of the grinding media, dopamine agonist, the optional liquid dispersion medium, and dispersing, wetting or other particle stabilizing agents present in the grinding vessel can vary within wide limits and depend on, for example, the size and density of the grinding media, the type of mill selected, the time of milling, etc. The process can be carried out in a continuous, batch or semibatch mode. In high energy media mills, it can be desirable to fill 80-95% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium or an anti-foaming agent may be added to the liquid dispersion.

The attrition time can vary widely and depends primarily upon the mechanical means and residence conditions selected, the initial and desired final particle size, among other factors. For roller mills, processing times from several days to weeks may be required. On the other hand, milling residence times of less than about 2 hours are generally required using high energy media mills. After attrition is completed, the grinding media is separated from the milled dopamine agonist particulate product (in either a dry or liquid dispersion form) using conventional separation techniques, such as by filtration, or sieving through a mesh screen.

To produce dopamine agonist particles having an effective particle size of less than about 1 micron, the grinding media can be made from beads having a size ranging from 0.05 mm to 4 mm. For example, high energy milling of dopamine agonist with yttrium stabilized zirconium oxide 0.4 mm beads for a milling residence time of 25 minutes to 1.5 hours in recirculation mode at 1200 to 3000 RPM. In another approach, high energy milling of dopamine agonist with 0.1 mm zirconium oxide balls for a milling residence time of 2 hours in batch mode can be used. The milling concentration can be from about 10% to about 30% dopamine agonist by weight in comparison to the milling slurry weight, which can contain a wetting and/or dispersing agent to coat the initial suspension so a uniform feed rate may be applied in continuous milling mode. Alternatively, batch milling mode is utilized with a milling media containing an agent to adjust viscosity and/or provide a wetting effect so that the dopamine agonist is well dispersed amongst the grinding media.

Microprecipitation to Obtain Dopamine Agonist Nanoparticles

Dopamine agonist particles can also be prepared by homogeneous nucleation and precipitation in the presence of a wetting agent or dispersing agent using methods analogous to those described in U.S. Pat. Nos. 5,560,932 and 5,665,331, which are specifically incorporated by reference. Such a method can include the steps of: (1) dispersing the dopamine agonist in a suitable liquid media: (2) adding the mixture from step (1) to a mixture including at least one dispersing agent or wetting agent such that at the appropriate temperature, the dopamine agonist is dissolved: and (3) precipitating the formulation from step (2) using an appropriate anti-solvent. The method can be followed by removal of any formed salt, if present, by dialysis or filtration and concentration of the dispersion by conventional means. In one embodiment, the dopamine agonist particles are present in an essentially pure form and dispersed in a suitable liquid dispersion media. In this approach the dopamine agonist particles are a discrete phase within the resulting mixture. Useful dispersing agents, wetting agents, solvents, and anti-solvents can be experimentally determined.

Homogenization to Obtain Dopamine Agonist Nanoparticles

Dopamine agonist particles can also be prepared by high pressure homogenization (see U.S. Pat. No. 5,510,118). In this approach dopamine agonist particles are dispersed in a liquid dispersion medium and subjected to repeated homogenization to reduce the particle size of the dopamine agonist particles to the desired effective average particle size. The dopamine agonist particles can be reduced in size in the presence of at least one or more dispersing agents or wetting agents. Alternatively, the dopamine agonist particles can be contacted with one or more dispersing agents or wetting agents either before or after attrition. Other materials, such as a diluent, can be added to the dopamine agonist/dispersing agent mixture before, during, or after the size reduction process. For example, unprocessed dopamine agonist can be added to a liquid medium in which it is essentially insoluble to form a premix (i.e., about 0.1-60% w/w dopamine agonist and about 20-60% w/w dispersing agents or wetting agents). The apparent viscosity of the premix suspension is preferably less than about 1000 centipoise. The premix can then be transferred to a microfluidizer and circulated continuously first at low pressures, and then at maximum capacity (i.e., 3.000 to 30,000 psi) until the desired particle size reduction is achieved. The resulting dispersion of dopamine agonist particles can be spray coated onto a sublingual pharmaceutical formulation of the invention using techniques well known in the art.

Milling with Simethicone

Foaming during the nanosizing can present formulation issues and can have negative consequences for particle size reduction. For example, high levels of foam or air bubbles in the mill can cause a drastic increase in viscosity rendering the milling process inoperable. Even a very low level of air presence can dramatically reduce milling efficiency causing the desired particle size unachievable. This may be due to the resultant air in the mill cushioning the milling balls and limiting grinding efficiency. The air also can form a microemulsion with the milled ingredients which presents many issues with respect to the delivery of an accurate dose and palatability. Addition of a small amount of simethicone is a very effective anti-foaming agent which minimizes milling variability or special handling techniques to avoid the introduction of air into the milling process.

The Use of Wetting and Dispersing Agents

The dopamine agonist particles can be prepared with the use of one or more wetting and/or dispersing agents, which are, e.g., adsorbed on the surface of the dopamine agonist particle. The dopamine agonist particles can be contacted with wetting and/or dispersing agents either before, during or after size reduction. Generally, wetting and/or dispersing agents fall into two categories: non-ionic agents and ionic agents. The most common non-ionic agents are excipients which are contained in classes known as binders, fillers, surfactants and wetting agents. Limited examples of non-ionic surface stabilizers are hydroxypropylmethylcellulose, polyvinylpyrrolidone, Plasdone, polyvinyl alcohol. Pluronics, Tweens and polyethylene glycols (PEGs). Ionic agents are typically organic molecules bearing an ionic bond such that the molecule is charged in the formulation, such as long chain sulfonic acid salts (e.g., sodium lauryl sulfate and dioctyl sodium sulfosuccinate).

Excipients, such as wetting and dispersing agents, can be applied to the surface of the dopamine agonist nanoparticulate via spray drying, spray granulation, or spray layering process. These procedures are well known in those skilled in the art. It is also common to add additional excipients prior to removal of solvent in the nanoparticulate suspension to aid in the dispersion of the solid composition in medium in which the solid composition will be exposed (e.g. saliva) to further prevent agglomeration and/or particle size growth of the small dopamine agonist particles. An example of such an additional excipient is a redispersing agent. Suitable redispersing agents include, without limitation, sugars, polyethylene glycols, urea and quartemary ammonium salts.

Therapy

Representative examples of diseases and conditions treatable using the sublingual formulations of the invention are as listed hereinabove, and include, but are not limited to, Parkinson's disease, sexual dysfunction, and depressive disorders, such as major depression and bipolar disorder.

Sublingual formulations of the invention include rapidly disintegrating or dissolving dosage forms, also known as fast dissolve, fast or rapid melt, and quick disintegrating dosage forms. These dosage forms dissolve or disintegrate rapidly in the patient's mouth without chewing or the need for water within a short time frame. Because of their ease of administration, such compositions are particularly useful for the specific needs of patients with compromised motor skills. The sublingual formulations may be in unit dosage form in the shape of, for example, a lozenge, a pill, a tablet, a film, or a strip. Alternatively, the sublingual formulations may be prepared in non-unit dosage forms, such as a gel.

The dopamine agonist may be administered in its free base form or as a pharmaceutically acceptable salt, such as a non-toxic acid addition salts or metal complexes that are commonly used in the pharmaceutical industry. Examples of acid addition salts include organic acids such as acetic, glucuronic, citric, lactic, pamoic, maleic, citric, malic, maleic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, alginic acid, polyacrylate, and copolymers of acrylate, methacrylate, and/or carboxymethyl polmer derivatives: and inorganic acid such as hydrochloric acid, hydrobromic acid, sulfuric acid phosphoric acid, or the like. Metal complexes include calcium, zinc, iron, and the like. In certain instances the formulation of the invention includes the hydrochloride salt of a dopamine agonist.

The formulations can be administered to patients in therapeutically effective amounts. For example, an amount is administered which prevents, reduces, or eliminates the symptoms of Parkinson's disease, sexual dysfunction, or depression, respectively. Typical dose ranges are from about 0.5 mg to about 30 mg of apomorphine, or a salt thereof, given up to five times per day. Typical dose ranges are from about 0.2 mg to about 20 mg of bromocriptine, or a salt thereof, given up to five times per day. Typical dose ranges are from about 0.2 mg to about 20 mg of cabergoline, or a salt thereof, given up to five times per day. Typical dose ranges are from about 0.3 mg to about 30 mg of dihydroergocryptine, or a salt thereof, given up to five times per day. Typical dose ranges are from about 0.05 mg to about 10 mg of lisuride, or a salt thereof, given up to five times per day. Typical dose ranges are from about 0.5 mg to about 75 mg of piribedil, or a salt thereof, given up to five times per day. Typical dose ranges are from about 0.05 mg to about 10 mg of pergolide, or a salt thereof, given up to five times per day. Typical dose ranges are from about 0.1 mg to about 20 mg of pramipexole, or a salt thereof, given up to five times per day. Typical dose ranges are from about 0.1 mg to about 20 mg of rotigotine, or a salt thereof, given up to five times per day. Typical dose ranges are from about 0.1 mg to about 40 mg of rotigotine, or a salt thereof, given up to five times per day. The exemplary dosage of dopamine agonist to be administered is likely to depend on such variables as the type and extent of the condition, the overall health status of the particular patient, the particular dopamine agonist being administered, and the particular sublingual formulation being used.

Potential adverse effects can be ameliorated by administering apomorphine, or an apomorphine prodrug, in combination with an anti-emetic agent, such as nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride or diphenidol hydrochloride. In certain instances it may be desirable to incorporate the anti-emetic into the sublingual formulation for simultaneous administration in combination with apomorphine, or apomorphine prodrug.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1—Monolayer and Bilayer Films

Films A-H, J, K, and L were prepared as described below. Films A-H were prepared using a solid particulate apomorphine hydrochloride having an effective particle size in the range of 125 μm to 250 μm.

Films J, K, and L were prepared using a solid particulate apomorphine hydrochloride that was processed to produce an effective particle size of about 8 μm. For Films J. K, and L apomorphine hydrochloride was milled using a Jet-Pulverizer 2 Micron-Master cyclone discharge mill with stainless steel liner. Nitrogen was used as the process gas at a pressure of 100 PSI and temperature of 25-45° C. The apomorphine hydrochloride was fed into the mill using a "V" groove vibratory feeder and recovered in an integrated bottom collector to reduce material loss associated with a dust bag collector. The design of this milling unit is described in U.S. Pat. No. 3,559,895.

Film A.

Film A is a monolayer film containing the components and amounts listed in Table A. Film A was prepared by first mixing sodium metabisulfite, disodium EDTA, propylene glycol, maltodextrin, and sucralose with water, and stirring the mixture. Acetone and menthol were added to this solution, and the mixture stirred. Apomorphine hydrochloride was added, with stirring, forming a clear solution.

Hypromellose was added slowly with stirring until a uniform, clear, viscous liquid was produced. The resulting mixture was placed under vacuum to eliminate air bubbles, cast as a uniform layer onto an inert support, and dried in an oven. The resulting dried film was clear in appearance.

TABLE A

| Component | bulk liquid mg/100 mg | dry film mg/100 mg | dry film mg |
|---|---|---|---|
| water | 39.8794 | — | — |
| acetone | 39.8247 | — | — |
| sodium metabisulfite | 0.1693 | 0.8342 | 0.5422 |
| disodium EDTA | 0.1693 | 0.8342 | 0.5422 |
| apomorphine HCl | 4.6845 | 23.0810 | 15.0027 |
| menthol | 1.1400 | 5.6169 | 3.6510 |
| propylene glycol | 2.2899 | 11.2826 | 7.3337 |
| maltodextrin M180 | 3.6340 | 17.9051 | 11.6383 |
| sucralose | 0.5526 | 2.7227 | 1.7698 |

TABLE A-continued

| Component | bulk liquid mg/100 mg | dry film mg/100 mg | dry film mg |
|---|---|---|---|
| Methocel E50 | 4.3210 | 21.2900 | 13.8385 |
| Methocel E5 | 3.3353 | 16.4334 | 10.6817 |
| Total mass, mg | 100.0000 | 100.0000 | 65.0000 |

Film B.

Film B is a monolayer film containing the components and amounts listed in Table B. Film B was prepared by first mixing sodium metabisulfite, disodium EDTA, glycerin, maltodextrin, and sucralose with water, and stirring the mixture. Acetone and menthol were added to this solution, and the mixture stirred.

Apomorphine hydrochloride was added and stirred, forming an opaque dispersion. Hypromellose was added slowly with stirring until a uniform, opaque, viscous liquid was produced. The resulting mixture was placed under vacuum to eliminate air bubbles, cast as a uniform layer onto an inert support, and dried in an oven. The resulting dried film was opaque white in color.

TABLE B

| Component | bulk liquid mg/100 mg | dry film mg/100 mg | dry film mg |
|---|---|---|---|
| water | 33.3333 | — | — |
| acetone | 33.3333 | — | — |
| sodium metabisulfite | 0.3280 | 0.9841 | 0.2460 |
| disodium EDTA | 0.3377 | 1.0130 | 0.2533 |
| apomorphine HCl | 20.0000 | 60.0000 | 15.0000 |
| menthol | 3.0565 | 9.1694 | 2.2924 |
| glycerin | 1.7945 | 5.3835 | 1.3459 |
| Maltrin M180 | 0.8548 | 2.5644 | 0.6411 |
| sucralose | 1.0613 | 3.1838 | 0.7959 |
| Methocel E50 | 2.2696 | 6.8087 | 1.7022 |
| Methocel E5 | 3.6310 | 10.8931 | 2.7233 |
| Total mass, mg | 100.0000 | 100.0000 | 25.0000 |
| Theoretical solids, % | 33.3334 | — | — |

Film C.

Film C is a bilayer film formed from an apomorphine layer containing the components and amounts listed in Table C1 and a neutralizing layer containing the components and amounts listed in Table C2.

Apomorphine layer C1 was prepared by first mixing sodium metabisulfite, disodium EDTA, glycerin, maltodextrin, and sucralose with water, and stirring the mixture. Acetone and menthol were added to this solution, and the mixture stirred. Apomorphine hydrochloride was added and stirred, forming an opaque dispersion. Hypromellose was added slowly with stirring until a uniform, opaque, viscous liquid was produced. The resulting mixture was placed under vacuum to eliminate air bubbles, cast as a uniform layer onto an inert support, and dried in an oven. The resulting dried film was opaque white in color.

TABLE C1

| Component | bulk liquid mg/100 mg | dry film mg/100 mg | dry film mg |
|---|---|---|---|
| water | 33.3333 | — | — |
| acetone | 33.3333 | — | — |
| sodium metabisulfite | 0.3280 | 0.9841 | 0.2460 |
| disodium EDTA | 0.3377 | 1.0130 | 0.2533 |
| apomorphine HCl | 20.0000 | 60.0000 | 15.0000 |
| menthol | 3.0565 | 9.1694 | 2.2924 |
| glycerin | 1.7945 | 5.3835 | 1.3459 |
| Maltrin M180 | 0.8548 | 2.5644 | 0.6411 |
| sucralose | 1.0613 | 3.1838 | 0.7959 |
| Methocel E50 | 2.2696 | 6.8087 | 1.7022 |
| Methocel E5 | 3.6310 | 10.8931 | 2.7233 |
| Total mass, mg | 100.0000 | 100.0000 | 25.0000 |
| Theoretical solids, % | 33.3334 | — | — |

Neutralizing layer C2 was prepared by slowly adding sodium carboxymethyl cellulose to water with stirring until a uniform, clear, viscous liquid is produced. Sodium phosphate tribasic, sodium phosphate dibasic, sodium metabisulfite, disodium EDTA, glycerin, and maltodextrin were then all added, and the mixture was stirred. Acetone was added to this solution, and the mixture was stirred, until a uniform, clear, viscous liquid was produced. The resulting mixture was placed under vacuum to eliminate air bubbles, cast as a uniform layer onto an inert support, and dried in an oven. The resulting dried layer was clear in appearance.

TABLE C2

| Component | bulk liquid mg/100 mg | dry film mg/100 mg | dry film mg |
|---|---|---|---|
| water | 70.0000 | — | — |
| acetone | 10.0000 | — | — |
| sodium phosphate tribasic ($Na_3PO_4$) | 3.3480 | 16.7400 | 1.6740 |
| disodium phosphate dibasic ($Na_2HPO_4$) | 0.5580 | 2.7900 | 0.2790 |
| sodium metabisulfite | 0.2158 | 1.0792 | 0.1079 |
| disodium EDTA | 0.1835 | 0.9174 | 0.0917 |
| glycerin | 1.9256 | 9.6280 | 0.9628 |
| Maltrin M180 | 5.2000 | 26.0000 | 2.6000 |
| sodium CMC, 7L2P | 8.5691 | 42.8454 | 4.2845 |
| Total mass, mg | 100.0000 | 100.0000 | 10.0000 |
| Theoretical solids, % | 20.0000 | — | — |

The apomorphine layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and packaged into individual foil pouches. The resulting dried bilayer film was opaque white in color.

Film D.

Film D is a bilayer film formed from an apomorphine layer containing the components and amounts listed in Table D1 and a neutralizing layer containing the components and amounts listed in Table D2.

Apomorphine layer D1 was prepared by slowly adding hydroxyethyl cellulose and hypromellose to water with stirring until a uniform, clear, viscous liquid was produced. Sodium metabisulfite, disodium EDTA, glycerin, maltodextrin, and sucralose were then all added, and the mixture stirred. Acetone and menthol were then added to this solution, and the mixture stirred. Apomorphine hydrochloride was then added and the mixture stirred, forming an opaque dispersion. The resulting mixture was placed under vacuum to eliminate air bubbles, cast as a uniform layer onto an inert support, and dried in an oven. The resulting dried layer was opaque white in color.

TABLE D1

| Component | bulk liquid mg/100 mg | dry film mg/100 mg | dry film mg |
|---|---|---|---|
| water | 38.6792 | — | — |
| acetone | 14.1509 | — | — |
| sodium metabisulfite | 0.4688 | 0.9939 | 0.4290 |
| disodium EDTA | 0.4643 | 0.9843 | 0.4249 |
| apomorphine HCl | 16.3912 | 34.7494 | 15.0000 |
| menthol | 2.5050 | 5.3105 | 2.2924 |
| glycerin | 4.3386 | 9.1978 | 3.9703 |
| Maltrin M180 | 19.2072 | 40.7194 | 17.5770 |
| sucralose | 0.8698 | 1.8439 | 0.7959 |
| Natrosol 250 G | 1.2332 | 2.6145 | 1.1286 |
| Natrosol 250 L | 1.2332 | 2.6145 | 1.1286 |
| Methocel E5 | 0.4584 | 0.9718 | 0.4195 |
| Total mass, mg | 100.0000 | 100.0000 | 43.1662 |
| Theoretical solids, % | 47.1698 | — | — |

Neutralizing layer D2 was prepared by slowly adding hydroxyethyl cellulose to water with stirring until a uniform, clear, viscous liquid was produced. Sodium phosphate tribasic, sodium phosphate dibasic, sodium metabisulfite, disodium EDTA, glycerin, and maltodextrin were then all added, and the mixture stirred. Acetone was added to this solution, and the mixture stirred, until a uniform, clear, viscous liquid was produced. The resulting mixture was placed under vacuum to eliminate air bubbles, cast as a uniform layer onto an inert support, and dried in an oven. The resulting dried layer was clear in appearance.

TABLE D2

| Component | bulk liquid mg/100 mg | dry film mg/100 mg | dry film mg |
|---|---|---|---|
| water | 79.6754 | — | — |
| acetone | 5.8157 | — | — |
| sodium phosphate tribasic ($Na_3PO_4$) | 2.4339 | 16.7751 | 1.6775 |
| disodium phosphate dibasic ($Na_2HPO_4$) | 0.4056 | 2.7959 | 0.2796 |
| sodium metabisulfite | 0.1255 | 0.8652 | 0.0865 |
| disodium EDTA | 0.1067 | 0.7355 | 0.0735 |
| glycerin | 1.1199 | 7.7186 | 0.7719 |
| Maltrin M180 | 5.2342 | 36.0756 | 3.6076 |
| Natrosol 250 G | 3.3887 | 23.3562 | 2.3356 |
| Natrosol 250 L | 1.6944 | 11.6781 | 1.1678 |
| Total mass, mg | 100.0000 | 100.0000 | 10.0000 |
| Theoretical solids, % | 20.2179 | — | — |

The apomorphine layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and packaged into individual foil pouches. The resulting dried bilayer film was opaque white in color.

Film E.

Film E is a bilayer film formed from an apomorphine layer containing the components and amounts listed in Table E1 and a neutralizing layer containing the components and amounts listed in Table E2.

Apomorphine layer E1 was prepared by slowly adding hydroxyethyl cellulose and hypromellose to water with stirring until a uniform, clear, viscous liquid was produced. Sodium metabisulfite, disodium EDTA, glycerin, maltodextrin, and sucralose were then all added, and the mixture was stirred. Acetone and menthol were added to this solution, and the mixture was stirred. Apomorphine hydrochloride was then added with stirring, forming an opaque dispersion. The resulting mixture was placed under vacuum to eliminate air bubbles, cast as a uniform layer onto an inert support, and dried in an oven. The resulting dried layer was opaque white in color.

TABLE E1

| Component | bulk liquid mg/100 mg | dry film mg/100 mg | dry film mg |
|---|---|---|---|
| water | 38.6792 | — | — |
| acetone | 14.1509 | — | — |
| sodium metabisulfite | 0.4688 | 0.9939 | 0.4290 |
| disodium EDTA | 0.4643 | 0.9843 | 0.4249 |
| apomorphine HCl | 16.3912 | 34.7494 | 15.0000 |
| menthol | 2.5050 | 5.3105 | 2.2924 |
| glycerin | 4.3386 | 9.1978 | 3.9703 |
| Maltrin M180 | 19.2072 | 40.7194 | 17.5770 |
| sucralose | 0.8698 | 1.8439 | 0.7959 |
| Natrosol 250 G | 1.2332 | 2.6145 | 1.1286 |
| Natrosol 250 L | 1.2332 | 2.6145 | 1.1286 |
| Methocel E5 | 0.4584 | 0.9718 | 0.4195 |
| Total mass, mg | 100.0000 | 100.0000 | 43.1662 |
| Theoretical solids, % | 47.1698 | — | — |

Neutralizing layer E2 was prepared by slowly adding hydroxyethyl cellulose to water with stirring until a uniform, clear, viscous liquid was produced. Meglumine, sodium metabisulfite, disodium EDTA, glycerin, and maltodextrin were then all added, and the mixture stirred. Acetone was added to this solution, and the mixture stirred, until a uniform, clear, viscous liquid was produced. The resulting mixture was placed under vacuum to eliminate air bubbles, cast as a uniform layer onto an inert support, and dried in an oven. The resulting dried layer was clear in appearance.

TABLE E2

| Component | bulk liquid mg/100 mg | dry film mg/100 mg | dry film mg |
|---|---|---|---|
| water | 85.8172 | — | — |
| acetone | 1.7129 | — | — |
| meglumine | 5.1388 | 41.2092 | 10.3023 |
| sodium metabisulfite | 0.0370 | 0.2965 | 0.0741 |
| disodium EDTA | 0.0314 | 0.2520 | 0.0630 |
| glycerin | 1.0963 | 8.7913 | 2.1978 |
| Maltrin M180 | 0.6852 | 5.4946 | 1.3736 |
| Natrosol 250 G | 2.7407 | 21.9782 | 5.4946 |
| Natrosol 250 L | 2.7407 | 21.9782 | 5.4946 |
| Total mass, mg | 100.0000 | 100.0000 | 25.0000 |
| Theoretical solids, % | 12.4699 | — | — |

The apomorphine layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and packaged into individual foil pouches. The resulting dried bilayer film was opaque white in color.

Film F.

Film F is a bilayer film formed from an apomorphine layer containing the components and amounts listed in Table F1 and a neutralizing layer containing the components and amounts listed in Table F2.

Apomorphine layer F1 was prepared by slowly adding hydroxyethyl cellulose and hypromellose to water with stirring until a uniform, clear, viscous liquid was produced.

Sodium metabisulfite, disodium EDTA, glycerin, maltodextrin, and sucralose were then all added, and the mixture was stirred. Acetone and menthol were added to this solution, and the mixture stirred. Apomorphine hydrochloride was added with stirring, forming an opaque dispersion. The resulting mixture was placed under vacuum to eliminate air bubbles, cast as a uniform layer onto an inert support, and dried in an oven. The resulting dried layer was opaque white in color.

TABLE F1

| Component | bulk liquid mg/100 mg | dry film mg/100 mg | dry film mg |
|---|---|---|---|
| water | 55.2012 | — | — |
| acetone | 6.8337 | — | — |
| sodium metabisulfite | 0.3984 | 1.0495 | 0.2860 |
| disodium EDTA | 0.3984 | 1.0495 | 0.2860 |
| apomorphine HCl | 20.8956 | 55.0389 | 15.0000 |
| menthol | 2.6361 | 6.9436 | 1.8924 |
| glycerin | 2.7861 | 7.3385 | 2.0000 |
| Maltrin M180 | 3.4423 | 9.0671 | 2.4711 |
| sucralose | 0.8302 | 2.1867 | 0.5959 |
| Natrosol 250 L | 6.1328 | 16.1539 | 4.4025 |
| Methocel E5 | 0.4451 | 1.1723 | 0.3195 |
| | | | |
| Total mass, mg | 100.0000 | 100.0000 | 27.2534 |
| Theoretical solids, % | 37.9651 | — | — |

Neutralizing layer F2 was prepared by slowly adding hydroxyethyl cellulose to water slowly with stirring until a uniform, clear, viscous liquid was produced. Meglumine, sodium metabisulfite, disodium EDTA, glycerin, and maltodextrin were then all added, and the mixture was stirred. Acetone was added to this solution, and the mixture stirred, until a uniform, clear, viscous liquid was produced. The resulting mixture was placed under vacuum to eliminate air bubbles, cast as a uniform layer onto an inert support, and dried in an oven. The resulting dried layer was clear in appearance.

TABLE F2

| Component | bulk liquid mg/100 mg | dry film mg/100 mg | dry film mg |
|---|---|---|---|
| water | 60.8111 | — | — |
| acetone | 6.1425 | — | — |
| meglumine | 19.6561 | 59.4803 | 9.9630 |
| sodium metabisulfite | 0.1326 | 0.4012 | 0.0672 |
| disodium EDTA | 0.1127 | 0.3410 | 0.0571 |
| glycerin | 1.4742 | 4.4610 | 0.7472 |
| Maltrin M180 | 4.9140 | 14.8701 | 2.4907 |
| Natrosol 250 L | 6.7568 | 20.4464 | 3.4248 |
| | | | |
| Total mass, mg | 100.0000 | 100.0000 | 16.7500 |
| Theoretical solids, % | 33.0464 | — | — |

The apomorphine layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and packaged into individual foil pouches. The resulting dried bilayer film was opaque white in color.

Film G.

Film G is a bilayer film formed from an apomorphine layer containing the components and amounts listed in Table G1 and a neutralizing layer containing the components and amounts listed in Table G2.

Apomorphine layer G1 was prepared by slowly adding hydroxyethyl cellulose and hypromellose to water with stirring until a uniform, clear, viscous liquid was produced. Sodium metabisulfite, disodium EDTA, glycerin, maltodextrin, and sucralose were then all added, and the mixture was stirred. Acetone and menthol were added to this solution, and the mixture stirred. Apomorphine hydrochloride was added with stirring, forming an opaque dispersion. The resulting mixture was placed under vacuum to eliminate air bubbles, cast as a uniform layer onto an inert support, and dried in an oven. The resulting dried layer was opaque white in color.

TABLE G1

| Component | bulk liquid mg/100 mg | dry film mg/100 mg | dry film mg |
|---|---|---|---|
| water | 55.2012 | — | — |
| acetone | 6.8337 | — | — |
| sodium metabisulfite | 0.3984 | 1.0495 | 0.2860 |
| disodium EDTA | 0.3984 | 1.0495 | 0.2860 |
| apomorphine HCl | 20.8956 | 55.0389 | 15.0000 |
| menthol | 2.6361 | 6.9436 | 1.8924 |
| glycerin | 2.7861 | 7.3385 | 2.0000 |
| Maltrin M180 | 3.4423 | 9.0671 | 2.4711 |
| sucralose | 0.8302 | 2.1867 | 0.5959 |
| Natrosol 250 L | 6.1328 | 16.1539 | 4.4025 |
| Methocel E5 | 0.4451 | 1.1723 | 0.3195 |
| | | | |
| Total mass, mg | 100.0000 | 100.0000 | 27.2534 |
| Theoretical solids, % | 37.9651 | — | — |

Neutralizing layer G2 was prepared by slowly adding hydroxyethyl cellulose to water with stirring until a uniform, clear, viscous liquid was produced. Sodium citrate, sodium metabisulfite, disodium EDTA, glycerin, and maltodextrin were all added, and the mixture was stirred. Acetone was added to this solution, and the mixture stirred, until a uniform, clear, viscous liquid is produced. The resulting mixture was placed under vacuum to eliminate air bubbles, cast as a uniform layer onto an inert support, and dried in an oven. The resulting dried layer was clear in appearance.

TABLE G2

| Component | bulk liquid mg/100 mg | dry film mg/100 mg | dry film mg |
|---|---|---|---|
| water | 68.5434 | — | — |
| acetone | 8.2782 | — | — |
| sodium citrate | 4.9669 | 21.4291 | 5.0358 |
| sodium metabisulfite | 0.1787 | 0.7709 | 0.1812 |
| disodium EDTA | 0.1519 | 0.6553 | 0.1540 |
| glycerin | 1.9868 | 8.5716 | 2.0143 |
| Maltrin M180 | 8.2782 | 35.7152 | 8.3931 |
| Natrosol 250 L | 7.6159 | 32.8579 | 7.7216 |
| | | | |
| Total mass, mg | 100.0000 | 100.0000 | 23.5000 |
| Theoretical solids, % | 23.1784 | — | — |

The apomorphine layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and packaged into individual foil pouches. The resulting dried bilayer film was opaque white in color.

Film H.

Film H is a bilayer film formed from an apomorphine layer containing the components and amounts listed in Table H1 and a neutralizing layer containing the components and amounts listed in Table H2.

Apomorphine layer H1 was prepared by slowly adding hydroxyethyl cellulose and hypromellose to water with stirring until a uniform, clear, viscous liquid was produced. Sodium metabisulfite, disodium EDTA, glycerin, maltodextrin, and sucralose were then all added, and the mixture was stirred. Acetone and menthol were added to this solution, and the mixture stirred. Apomorphine hydrochloride was added with stirring, forming an opaque dispersion. The resulting mixture was placed under vacuum to eliminate air bubbles, cast as a uniform layer onto an inert support, and dried in an oven. The resulting dried layer was opaque white in color.

TABLE H1

| Component | bulk liquid mg/100 mg | dry film mg/100 mg | dry film mg |
|---|---|---|---|
| water | 55.2012 | — | — |
| acetone | 6.8337 | — | — |
| sodium metabisulfite | 0.3984 | 1.0495 | 0.2860 |
| disodium EDTA | 0.3984 | 1.0495 | 0.2860 |
| apomorphine HCl | 20.8956 | 55.0389 | 15.0000 |
| menthol | 2.6361 | 6.9436 | 1.8924 |
| glycerin | 2.7861 | 7.3385 | 2.0000 |
| Maltrin M180 | 3.4423 | 9.0671 | 2.4711 |
| sucralose | 0.8302 | 2.1867 | 0.5959 |
| Natrosol 250 L | 6.1328 | 16.1539 | 4.4025 |
| Methocel E5 | 0.4451 | 1.1723 | 0.3195 |
| Total mass, mg | 100.0000 | 100.0000 | 27.2534 |
| Theoretical solids, % | 37.9651 | — | — |

Neutralizing layer H2 was prepared by slowly adding hydroxyethyl cellulose to water with stirring until a uniform, clear, viscous liquid was produced. Meglumine, sodium citrate, sodium metabisulfite, disodium EDTA, glycerin, and maltodextrin were then all added, and the mixture stirred. Acetone was added to this solution, and the mixture stirred, until a uniform, clear, viscous liquid was produced. The resulting mixture was placed under vacuum to eliminate air bubbles, cast as a uniform layer onto an inert support, and dried in an oven. The resulting dried layer was clear in appearance.

TABLE H2

| Component | bulk liquid mg/100 mg | dry film mg/100 mg | dry film mg |
|---|---|---|---|
| water | 60.2192 | — | — |
| acetone | 6.0828 | — | — |
| meglumine | 14.4769 | 42.9608 | 5.0049 |
| sodium citrate | 5.9611 | 17.6897 | 2.0609 |
| sodium metabisulfite | 0.1313 | 0.3896 | 0.0454 |
| disodium EDTA | 0.1116 | 0.3312 | 0.0386 |
| glycerin | 1.4599 | 4.3322 | 0.5047 |
| Maltrin M180 | 4.8662 | 14.4406 | 1.6823 |
| Natrosol 250 L | 6.6910 | 19.8558 | 2.3132 |
| Total mass, mg | 100.0000 | 100.0000 | 11.6500 |
| Theoretical solids, % | 33.6980 | — | — |

The apomorphine layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and packaged into individual foil pouches. The resulting dried bilayer film was opaque white in color.

Film J

Film J is a bilayer film formed from an apomorphine layer containing components and amounts listed in Table J1 and a neutralizing layer containing the components and amounts listed in Table J2.

The apomorphine layer J1 was prepared by adding hydroxyethyl cellulose and hypromellose to water slowly while stirring until a uniform, clear, viscous liquid is produced. Sodium metabisulfite, disodium EDTA dihydrate, glycerin, maltodextrin, and sucralose were then added, and the mixture was stirred. Acetone, glyceryl monostearate and menthol were then added to the solution, and the mixture was stirred. Apomorphine hydrochloride was then added, with stirring, forming an opaque dispersion. The resulting mixture was placed under vacuum to eliminate air bubbles. The viscous liquid was then cast as a uniform layer onto an inert support and dried in an oven. The resulting dried layer was opaque white in color.

TABLE J1

| Component | bulk liquid mg/100 mg | dry film mg/100 mg | dry film mg |
|---|---|---|---|
| water | 36.9736 | — | — |
| acetone | 14.2616 | — | — |
| sodium metabisulfite | 0.4551 | 0.9332 | 0.4179 |
| disodium EDTA, dihydrate | 0.4714 | 0.9667 | 0.4329 |
| apomorphine HCl | 16.3345 | 33.4966 | 15.0000 |
| menthol | 2.4973 | 5.1211 | 2.2933 |
| glyceryl monostearate | 0.4770 | 0.9781 | 0.4380 |
| glycerin | 4.4518 | 9.1292 | 4.0881 |
| maltodextrin M180 | 18.6597 | 38.2647 | 17.1352 |
| sucralose | 0.8512 | 1.7454 | 0.7816 |
| Natrosol 250 L | 4.1082 | 8.4245 | 3.7725 |
| Methocel E5 | 0.4587 | 0.9405 | 0.4212 |
| Total mass, mg | 100.0000 | 100.0000 | 44.7807 |
| Theoretical solids | 48.7% | — | — |

TABLE J2

| Component | bulk liquid mg/100 mg | dry film mg/100 mg | dry film mg |
|---|---|---|---|
| water | 60.68455 | — | — |
| acetone | 6.2112569 | — | — |
| meglumine | 19.594899 | 59.1916 | 9.9146 |
| sodium metabisulfite | 0.1395251 | 0.4215 | 0.0706 |
| disodium EDTA, dihydrate | 0.1164038 | 0.3516 | 0.0589 |
| glycerin | 1.6141056 | 4.8758 | 0.8167 |
| maltodextrin M180 | 4.8965322 | 14.7913 | 2.4775 |
| Natrosol 250 L | 6.7427278 | 20.3682 | 3.4117 |
| Total mass, mg | 100.0000 | 100.0000 | 16.7500 |
| Theoretical solids, % | 33.1042 | — | — |

Neutralizing layer J2 was prepared by adding hydroxyethyl cellulose to water slowly with stirring until a uniform, clear, viscous liquid was produced. Meglumine, sodium metabisulfite, disodium EDTA dihydrate, glycerin, and maltodextrin were then added, and the mixture was stirred. Acetone was added to this solution, and the mixture was stirred, until a uniform, clear, viscous liquid was produced. The resulting mixture was placed under vacuum to eliminate air bubbles. The viscous liquid was then cast as a uniform layer onto an inert support and dried in an oven. The resulting dried layer was clear in appearance.

The separate Apomorphine hydrochloride layer and neturalizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and subsequently packaged into individual foil pouches. The resulting dried bilayer film was opaque white in color.

Film K

Film K is a bilayer film formed from an apomorphine layer containing components and amounts listed in Table K1 and a neutralizing layer containing the components and amounts listed in Table K2.

The apomorphine layer K1 was prepared by adding hydroxyethyl cellulose and hypromellose to water slowly while stirring until a uniform, clear, viscous liquid is produced. Sodium metabisulfite, disodium EDTA dihydrate, glycerin, maltodextrin, and sucralose were then added, and the mixture was stirred. Acetone, glyceryl monostearate and menthol were then added to the solution, and the mixture was stirred. Apomorphine hydrochloride was then added, with stirring, forming an opaque dispersion. The resulting mixture was placed under vacuum to eliminate air bubbles. The viscous liquid was then cast as a uniform layer onto an inert support and dried in an oven. The resulting dried layer was opaque white in color.

TABLE K1

| Component | bulk liquid mg/100 mg | dry film mg/100 mg | dry film mg |
|---|---|---|---|
| water | 36.9736 | — | — |
| acetone | 14.2616 | — | — |
| sodium metabisulfite | 0.4551 | 0.9332 | 0.4179 |
| disodium EDTA, dihydrate | 0.4714 | 0.9667 | 0.4329 |
| apomorphine HCl | 16.3345 | 33.4966 | 15.0000 |
| menthol | 2.4973 | 5.1211 | 2.2933 |
| glyceryl monostearate | 0.4770 | 0.9781 | 0.4380 |
| glycerin | 4.4518 | 9.1292 | 4.0881 |
| maltodextrin M180 | 18.6597 | 38.2647 | 17.1352 |
| sucralose | 0.8512 | 1.7454 | 0.7816 |
| Natrosol 250 L | 4.1082 | 8.4245 | 3.7725 |
| Methocel E5 | 0.4587 | 0.9405 | 0.4212 |
| Total mass, mg | 100.0000 | 100.0000 | 44.7807 |
| Theoretical solids | 48.7% | — | — |

TABLE K2

| Component | bulk liquid mg/100 mg | dry film mg/100 mg | dry film mg |
|---|---|---|---|
| water | 60.7040 | — | — |
| acetone | 6.2195 | — | — |
| pyridoxine HCl | 19.6039 | 59.2684 | 9.9275 |
| sodium hydroxide | 3.3010 | 9.9800 | 1.6716 |
| sodium metabisulfite | 0.1356 | 0.4100 | 0.0687 |
| disodium EDTA, dihydrate | 0.1205 | 0.3642 | 0.0610 |
| glycerin | 1.6617 | 5.0238 | 0.8415 |
| maltodextrin M180 | 1.5089 | 4.5619 | 0.7641 |
| Natrosol 250 L | 6.7449 | 20.3918 | 3.4156 |
| Total mass, mg | 100.0000 | 100.0000 | 16.7500 |
| Theoretical solids, % | 33.0765 | — | — |

Neutralizing layer K2 was prepared by adding hydroxyethyl cellulose to water slowly with stirring until a uniform, clear, viscous liquid was produced. Sodium hydroxide, pyridoxine HCl, sodium metabisulfite, disodium EDTA dihydrate, glycerin, and maltodextrin were then added, and the mixture was stirred. Acetone was added to this solution, and the mixture was stirred, until a uniform, clear, viscous liquid was produced. The resulting mixture was placed under vacuum to eliminate air bubbles. The viscous liquid was then cast as a uniform layer onto an inert support and dried in an oven. The resulting dried layer was clear in appearance.

The separate Apomorphine hydrochloride layer and neturalizing layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and subsequently packaged into individual foil pouches.

The resulting dried bilayer film was opaque white in color.

Film L Film L is a bilayer film formed from an apomorphine layer containing components and amounts listed in Table L1 and a neutralizing layer containing the components and amounts listed in Table L2.

The apomorphine layer L1 was prepared by adding hydroxyethyl cellulose and hypromellose to water slowly while stirring until a uniform, clear, viscous liquid is produced. Sodium metabisulfite, disodium EDTA dihydrate, glycerin, maltodextrin, and sucralose were then added, and the mixture was stirred. Acetone, glyceryl monostearate and menthol were then added to the solution, and the mixture was stirred. Apomorphine hydrochloride was then added, with stirring, forming an opaque dispersion. The resulting mixture was placed under vacuum to eliminate air bubbles. The viscous liquid was then cast as a uniform layer onto an inert support and dried in an oven. The resulting dried layer was opaque white in color.

TABLE L1

| Component | bulk liquid mg/100 mg | dry film mg/100 mg | dry film mg |
|---|---|---|---|
| water | 36.9736 | — | — |
| acetone | 14.2616 | — | — |
| sodium metabisulfite | 0.4551 | 0.9332 | 0.4179 |
| disodium EDTA, dihydrate | 0.4714 | 0.9667 | 0.4329 |
| apomorphine HCl | 16.3345 | 33.4966 | 15.0000 |
| menthol | 2.4973 | 5.1211 | 2.2933 |
| glyceryl monostearate | 0.4770 | 0.9781 | 0.4380 |
| glycerin | 4.4518 | 9.1292 | 4.0881 |
| maltodextrin M180 | 18.6597 | 38.2647 | 17.1352 |
| sucralose | 0.8512 | 1.7454 | 0.7816 |
| Natrosol 250 L | 4.1082 | 8.4245 | 3.7725 |
| Methocel E5 | 0.4587 | 0.9405 | 0.4212 |
| Total mass, mg | 100.0000 | 100.0000 | 44.7807 |
| Theoretical solids | 48.7% | — | — |

TABLE L2

| Component | bulk liquid mg/100 mg | dry film mg/100 mg | dry film mg |
|---|---|---|---|
| water | 60.6845 | — | — |
| acetone | 6.2113 | — | — |
| magnesium hydroxide | 2.5949 | 7.8386 | 1.6000 |
| sodium metabisulfite | 0.1395 | 0.4215 | 0.0860 |
| disodium EDTA, dihydrate | 0.1164 | 0.3516 | 0.0718 |
| glycerin | 2.6141 | 7.8966 | 1.6118 |

TABLE L2-continued

| Component | bulk liquid mg/100 mg | dry film mg/100 mg | dry film mg |
|---|---|---|---|
| maltodextrin M180 | 13.8965 | 41.9782 | 8.5685 |
| Natrosol 250 L PHARM | 13.7427 | 41.5136 | 8.4737 |
| Total mass, mg | 100.0000 | 100.0000 | 20.4119 |
| Theoretical solids, % | 33.1042 | — | — |

Neutralizing layer L2 was prepared by adding hydroxyethyl cellulose to water slowly with stirring until a uniform, clear, viscous liquid was produced. Sodium metabisulfite, disodium EDTA dihydrate, glycerin, maltodextrin, and magnesium hydroxide were all added, and the mixture was stirred. Acetone was added to this solution, and the mixture was stirred, until a uniform, opaque, viscous dispersion was produced. The resulting mixture was placed under vacuum to eliminate air bubbles. The viscous liquid was then cast as a uniform layer onto an inert support and dried in an oven. The resulting dried layer was translucent white in appearance.

The separate Apomorphine hydrochloride layer and pH regulating layer were laminated together by applying a spray of ethanol between them. This bilayer construction, sandwiched between two inert supports, was dried in an oven. The dried bilayer was removed from the inert supports, cut into unit-dose films of a predetermined size (22 mm×22 mm), and subsequently packaged into individual foil pouches. The resulting dried bilayer film was opaque white in color.

Example 2—Pharmacokinetics

Food was withheld from the animals for a minimum of 12 hours prior to study initiation and four hours post dose. Prior to dosing, animals were weighed and assigned to experimental groups, stratified according to body weight. Animals manifesting poor or irregular appetite prior to study were excluded. For sublingual administration of the test article, animals were placed in induction chamber and anesthetized with isoflurane using a face mask. The test article was placed under the tongue and the animal's mouth was closed, while it was also maintained under anesthesia. Five minutes post administration, the animal was released. Blood samples were collected predosing, and at 10 minutes. 20 minutes, 30 minutes. 1 hour, 2 hours, and 4 hours post test article administration via a percutaneous catheter in the auricular artery. Blood samples were stabilized and kept cold until analysis. Bioassays were performed using C18RP-HPLC-MS. PK parameters for various formulations were calculated using a non-compartmental (trapezoid) model and are provided in Table 1 and Table 2 below.

TABLE 1

PK of films A, B, C, D, and E.

| PK values | sc inj[a] | A | B | C | D | E |
|---|---|---|---|---|---|---|
| Dose administered (mg/kg) | 0.5 | 0.28 | 0.28 | 0.28 | 0.28 | 0.28 |
| N = | 6 | 5 | 5 | 5 | 5 | 5 |
| $C_{max}$ (ng/mL) | 331 | 116 | 117 | 39 | 104 | 166 |
| $T_{max}$ (minutes) | 25 | 20 | 32 | 10 | 35 | 32 |
| $AUC_{inf}$ (ng/mL · minute) | 17828 | 10142 | 8150 | 1107 | 8707 | 11967 |
| Bioavailability (%)[b] | 100 | 96 | 77 | 10 | 87 | 109 |

[a]Literature value.
[b]Relative to 100% bioavailability for administration by subcutaneous injection.

TABLE 2

PK of films F, G, H, J, and K.

| PK values | sc inj[a] | F | G | H | J | K |
|---|---|---|---|---|---|---|
| Dose administered (mg/kg) | 0.5 | 0.28 | 0.28 | 0.28 | 0.28 | 0.28 |
| N =[b] | 6 | 4 | 5 | 5 | 8 | 8 |
| $C_{max}$ (ng/mL) | 331 | 94 | 132 | 91 | 107 | 100 |
| $T_{max}$ (minutes) | 25 | 25 | 40 | 28 | 13 | 14 |
| $AUC_{inf}$ (ng/mL · minute) | 17828 | 6210 | 9511 | 6285 | 5019 | 5680 |
| Bioavailability (%)[c] | 100 | 61 | 82 | 66 | 57 | 65 |

[a]Literature value.
[b]Number of rabbits tested (for Film F, 5 rabbits were dosed, but one data point was rejected as an outlier (>2 SD from mean).
[c]Relative to 100% bioavailability for administration by subcutaneous injection.

Film A (the only film that includes propylene glycol) incorporates the apomorphine hydrochloride dissolved in the monolayer at high concentration, and exhibits rapid dissolution, and rapid initial uptake. Preliminary stability suggests lower stability than that observed for Film B (a glycerol monolayer formulation that includes crystalline apomorphine hydrochloride).

Film C combines the apomorphine layer of Film B with a pH neutralizing layer containing carboxymethyl cellulose and inorganic phosphate as a base. Five minutes after dosing in the rabbit with Film C, a large portion of the film was recovered. Analysis showed it to be the apomorphine layer undissolved. We determined that the apomorphine layer does not dissolve well in phosphate buffer, which explains the low AUC and $C_{max}$ observed for this formulation. The rapid $T_{max}$ observed for Film C appears to be an artifact of the poor dissolution of the apomorphine layer.

Films D and E were designed to dissolve more rapidly by including a large portion of hydrolyzed starch as a disintegrant. In the case of Film E, the phosphate was replaced with an organic base (meglumine) to minimize interference with the dissolution of the apomorphine layer. Film D exhibited slower uptake and higher variability (rabbit to rabbit) than Films A or B. Film E was superior to Film D, but exhibited slower uptake than Films A and B.

In Films F, G, and H, the amount of apomorphine hydrochloride in the apomorphine layer was increased to 55% (w/w). Films F. G, and H utilize an organic base (i.e., meglumine for Film F; citrate for Film G, and a mixture of meglumine and citrate for Film H).

Film F exhibited a lower AUC and $C_{max}$, slightly shorter $T_{max}$, and less variability.

In contrast, Film G exhibited high AUC and $C_{max}$ values, but a longer $T_{max}$ and higher variability than Film F.

Film H performed similarly to Film F.

To assess the impact of water on the pharmacokinetic parameters, we added 200 µl water to the rabbit's mouth after dosing with Film H. We observed that AUC and $C_{max}$ increased, but $T_{max}$ increased as well. Water did not help to accelerate absorption at early time points.

Mineral (inorganic) pH neutralizers seem to lead to lower $C_{max}$, higher $T_{max}$ and higher variability. Citrate seems to be better tolerated than phosphate. Meglumine appears to give best results.

Films E, F, H, J, and K exhibit pharmacokinetic parameters closest to a subcutaneous injection (best peak shape) after dose adjustment (i.e., using larger quantities of apomorphine hydrochloride), with Films J and K demonstrating the fastest $T_{max}$ values and PK values closest to those observed for subcutaneous injection of apomorphine hydrochloride.

All the bilayers have about the same initial rate of absorption (i.e., 40 ng/ml in blood at 10 minutes post dosing).

We have observed that the monolayers have the fastest initial onset of absorption. This is surprising given the fact that the drug is protonated (see Example 6). Since the neutral apomorphine has a much higher rate of permeability than the protonated form, we can conclude that absorption of the monolayer is accompanied by release of the hydrochloride salt from the apomorphine and into the tissue. Since HCl is potential irritant when left unbuffered (saliva is unbuffered), increasing pH may avoid any tissue irritation and so the use of a pH neutralizer (i.e., to a pH of 2.5 to 5.5) may be desired.

All dosing has been with the sublingual film placed against the bottom of the mouth (not on the underside of tongue) and with apomorphine layer in direct contact with the tissues.

Example 3—Dispersed Milled Apomorphine in Bilayer Film

Using methods analogous to those described in Example 1, a jet-milled powder of apomorphine hydrochloride (D95<20 µm) is added, along with the other components of the apomorphine layer, to a mixture of ethanol and ethylacetate to create a homogeneous dispersion. The mixture is spread on a thin plastic liner and dried to produce a film. This film can be administered as is or combined with a neutralizing layer as per Example 1. Also contemplated, is the addition of jet-milled pH neutralizing agent to the neutralizing layer either for inclusion with the apomorphine (i.e., to produce a single layer wherein both active apomorphine hydrochloride and a neutralizing agent are dispersed as solid agents within a single layer), or to a neutralizing layer (i.e., to form a bilayer film).

Example 4—Dosage Forms Including Permeation Enhancers

Using methods analogous to those described in Example 1, from 0.2 to 2% (w/w) permeation enhancer is included in the apomorphine layer of any of films A-H, or, optionally, in both layers of the bilayer film. The permeation enhancer can be glycerol monostearate, or any permeation enhancer described herein.

Example 5—Permability Studies

Freshly collected buccal tissues were obtained from pig and mucosa's were isolated carefully.

The prepared mucosa membranes with approximate size of 4 cm² were mounted between donor and receiver chambers of Franz diffusion cells with available diffusion area of 1.77 cm². Test treatments and controls were run in quadruplicate. The receiver compartment, which contained a stirring bar, was filled with 8 mL of KRB buffer, pH 7.4 containing 1% BSA. The Franz cells were placed in a heating/stirring block. The temperature was set at 37° C. in order to maintain the tissue surface temperature at 32° C.; the stirring rate was set at 400 rpm. Two milliliters of formulated compound at different pHs was added to the donor chambers, completely covering the exposed mucosa. All dosing solutions contained 0.1% of sodium dithionite, 0.2% DMSO and 5% propylene glycol or glycerin. The donor compartment was covered with Parafilm to minimize evaporation. An aliquot (~0.5 mL) was taken from the receiver compartment at 2, 60, 90, and 120 min and replaced with an equal volume of buffer warmed at 37° C. Sampling time points from donor compartment were 0, 60, 90 and 120 min. Samples were diluted with 0.5 mL (1:1) of 10% aq. ascorbic acid. The concentration of each analyte was quantified by LC-MS/MS (Appendix I). The whole study was done in dark with yellow light, and glass vials and syringes were used for sampling. The apparent permeability coefficient (Papp), total amount of flux and percent recovery of control and test compounds were calculated as follows:

$Papp = (dCr/dt) \cdot Vr / (A \cdot C0)$

Normalized $Papp = (dCr/dt) \cdot Vr / (A \cdot (Cd\ initial + Cd\ final)/2)$ $Flux = (dCr/d) \cdot Vr / (A)$ Percent Recovery = $100 \cdot ((Vr \cdot Cr\ final) + (Vd \cdot Cd\ final)) / (Vd \cdot C0)$ In the above equations, $dC_r/dt$ is the slope of the cumulative receiver compartment concentration versus time, µM·min-1; A is the diffusional surface area of the exposed skin membrane, 1.77 cm²; $V_r$ is the volume of the receiver compartment, 8.0 mL; $V_d$ is the volume of the donor compartment, 2.0 mL; $C_r$ is the cumulative receiver compartment concentration in µM; $C_0$ is the concentration of the donor at 0 minutes of the incubation, µM; $C_{r\ initial}$ is the concentration of the receiver at the end of the incubation period, µM: $C_{d\ initial}$ is the concentration of the donor at the beginning of the incubation period (interval), µM. $C_{d\ final}$ is the concentration of the donor at the end of the incubation period (interval), µM. The results are tabulated below.

| Treatement tested | Papp |
|---|---|
| pH 6.4 | 0.071 |
| pH 6.8 | 0.054 |
| pH 7.4 | 0.185 |
| pH 8.0 | 0.556 |
| pH 8.0 + 1% glycerin monostearate | 2.34 |
| pH 8.0 + 1% magnesium stearate | 0.3 |
| pH 8.0 + 1% tocopherol acetate | 0.98 |

Glycerin monostearate and tocopherol acetate increase the apparent rate of permeability through excised buccal tissue, while magnesium stearate retards permeation.

Example 6—Ropinerol Bilayer Film

A bilayer film is formed from an ropinerol containing the components and amounts listed in Table R1 and a neutralizing layer containing the components and amounts listed in Table R2.

The API Layer R1 is prepared by slowly adding hydroxyethyl cellulose and hypromellose to water with stirring until a uniform, clear, viscous liquid is produced. Disodium EDTA, glycerin, maltodextrin, and sucralose are then all added, and the mixture is stirred. Acetone and menthol are added to this solution, and the mixture is stirred. Ropinerol hydrochloride is then added with stirring, forming an opaque dispersion. The resulting mixture is placed under vacuum to eliminate air bubbles, cast as a uniform layer onto an inert support and dried in an oven.

TABLE R1

| Component | bulk liquid mg/100 mg | dry film mg/100 mg | dry film mg |
|---|---|---|---|
| Water | 38.6792 | — | — |
| Acetone | 14.1509 | — | — |
| disodium EDTA | 0.4643 | 0.9843 | 0.4249 |
| ropinerol HCl | 16.3912 | 34.7494 | 15.0000 |
| menthol | 2.5050 | 5.3105 | 2.2924 |
| glycerin | 4.3386 | 9.1978 | 3.9703 |
| Maltrin M180 | 19.2072 | 40.7194 | 17.5770 |
| sucralose | 0.8698 | 1.8439 | 0.7959 |
| Natrosol 250 G | 1.2332 | 2.6145 | 1.1286 |
| Natrosol 250 L | 1.2332 | 2.6145 | 1.1286 |
| Methocel E5 | 0.4584 | 0.9718 | 0.4195 |
| Total mass, mg | 100.0000 | 100.0000 | 43.1662 |
| Theoretical solids, % | 47.1698 | — | — |

Neutralizing layer R2 is prepared by slowly adding hydroxyethyl cellulose to water with stirring until a uniform, clear, viscous liquid is produced. Pyridoxine, disodium EDTA, glycerin, and maltodextrin are then all added, and the mixture is stirred. Acetone is added to this solution, and the mixture stirred, until a uniform, clear, viscous liquid was produced. The resulting mixture is placed under vacuum to eliminate air bubbles, cast as a uniform layer onto an inert support, and dried in an oven.

TABLE R2

| Component | bulk liquid mg/100 mg | dry film mg/100 mg | dry film mg |
|---|---|---|---|
| water | 85.8172 | — | — |
| acetone | 1.7129 | — | — |
| pyridoxine | 5.1388 | 41.2092 | 10.3023 |
| sodium metabisulfite | 0.0370 | 0.2965 | 0.0741 |
| disodium EDTA | 0.0314 | 0.2520 | 0.0630 |
| glycerin | 1.0963 | 8.7913 | 2.1978 |
| Maltrin M180 | 0.6852 | 5.4946 | 1.3736 |
| Natrosol 250 G | 2.7407 | 21.9782 | 5.4946 |
| Natrosol 250 L | 2.7407 | 21.9782 | 5.4946 |
| Total mass, mg | 100.0000 | 100.0000 | 25.0000 |
| Theoretical solids, % | 12.4699 | — | — |

The dopamine agonist (ropinerol) layer and neutralizing layer were laminated together by applying a spray of ethanol between them. This bilayer construction, sandwiched between two inert supports, was dried in an oven. The dried bilayer was removed from the inert supports, cut into unit-dose films of a predetermined size and packaged into individual foil pouches. The resulting dried bilayer film was opaque white in color.

Example 7—Irritation Testing (General Method)

On Day 1. Adult Golden Syrian hamsters (approx 8 weeks of age and 100 grams), apportioned 36 control (18/sec) and 30 test article-treated (15/sex), are anesthetised. Approximately 1 cm² of the left buccal pouch cheek is abraded by manually scraping with a scalpel to remove surface layer of tissue without bleeding. On Day 2, test articles are applied to cheek pouches on both sides, abraded and non, at 9 am, 1 pm and 5 pm (t.i.d). Dosing is continued for a total of 28 days (ie, to Day 29). Control animals are treated similarly but with a control film applied to both cheek pouches. The control film is formulated as described above in the examples, but (i) without any dopamine agonist, (ii) without a pH neutralizing agent, and (iii) with sufficient acid (e.g., succinic acid, acetic acid, or an inorganic acid) to produce a pH of less than 3 following administration to, and dissolution in, the cheek pouch of an animal. Systemic signs, body weight and food consumption are recorded daily. Cheeks everted, cleared of food by washing with distilled water and gauze, and examined for signs of irritation prior to the first dose on Days 1, 2, 3, 4, 8, 14. & 21 and prior to necropsy on Day 29. Necropies are recorded on Day 2: 3 controls/sex: Day 5: 5 control & 5 treated animals/sex; Day 29: 5 controls & 5 treated animals/sex; Day 43: 5 controls & 5 treated animals/sex with examination of gross signs and histopathology of cheek pouches. Each animal can be monitored for both the extent of irritation following an administration. For abraded animals, the animals can be monitored for the amount of time required to observe healing in the cheek while receiving treatment.

The compositions of the invention can be non-irritating (e.g., performing equal to, or better than, a placebo formulation free of an acid addition salt of the active) as determined using the test described above.

Example 8—Stability of Packaged Films Including Apomorphine Hydrochloride

Films (see Example 1) were packaged individually in plastic-lined aluminum foils and thermally sealed to eliminate all contact with air or light. The films were tested for stability by placing the packaged films in an over at 40° C. After 2 months the color of the films was observed for any color change that would indicate oxidation of apomorphine to a quinone-type product, which are blue to green (see Rehse Achives des Pharmazie 1969, 7, 488). The results are provided in Table 3.

TABLE 3

| Film | 1 months at 40° C. | 2 months at 40° C. |
|---|---|---|
| A | Uncolored to light beige | Blue |
| B | Uncolored to light beige | Uncolored to light beige |
| C | Uncolored to light beige | Uncolored to light beige |
| D | Not tested | |
| E | uncolored | Light blue |
| F | Not tested | |
| G | uncolored | Light blue |
| H | Not tested | |
| J | uncolored | Light blue |
| K | uncolored | uncolored |

Example 9—Tissue Histology Studies

Animals (8 per group) were dosed 3 times with either bilayer Film J or Film K (7 mm disk. 1.1 mg apomorphine hydrochloride prepared according to Example 1) with an interval of 2 hours between dosing. With each dose administered. 500 μl of water was added to the sublingual region immediately after administering the dose to mimic salivation. Approximately 4 hours after the last dose, animals were euthanized, the tongue and the adjacent sublingual tissue were harvested and immediately fixed by placing in 10% formalin. Tissues were processes and embedded in paraffin, sectioned and stained with hematoxylin and eosin (H&E). Three sections of the tongue and sublingual tissues were trimmed and processed. Histological slides were made from the tissue to slide from each animal to include right, midline and left sections to ensure that the dose application site was examined microscopically. Resulting slides were examined.

There were no macroscopic observations (i.e., there was no evidence of irritation) due to the test article. In all slides, there were no microscopic findings in either group relating to the application of bilayer test strips. There is no evidence of local irritation related to multidose application of the strip according to the procedure.

Example 10—Bilayer Films Prepared for Clinical Studies

Placebo (film M) and API (film N) bilayer films were prepared as described below for use in clinical studies.

Placebo Film (M1)

The placebo film is a bilayer film formed without apomorphine and contains components and amounts listed in Table M1 and a neutralizing layer containing the components and amounts listed in Table M2.

The apomorphine layer M1 was prepared by combining acetone, glyceryl monostearate, and menthol with stirring until a uniform, clear solution was produced. Water was added, and the mixture was stirred. Hypromellose was then added to this solution slowly with stirring until a uniform, clear liquid was produced. Sodium metabisulfite and disodium EDTA dihydrate were then added, with stirring until a uniform liquid was produced. Hydroxyethyl cellulose was added to this solution slowly with stirring until a uniform, clear, viscous liquid was produced. Glycerin, maltodextrin, and sucralose were then added with stirring until a uniform, clear, viscous liquid was produced. The resulting mixture was placed under vacuum to eliminate air bubbles. The viscous liquid was then cast as a uniform layer onto an inert support and dried in an oven. The resulting dried layer was clear/hazy in appearance.

TABLE M1

| Component | bulk liquid mg/100 mg | dry film mg/100 mg | dry film mg |
|---|---|---|---|
| water | 60.9548 | — | — |
| acetone | 11.0307 | — | — |
| sodium metabisulfite | 0.5522 | 1.9710 | 0.4820 |
| disodium EDTA, dihydrate | 0.5555 | 1.9830 | 0.4849 |
| menthol | 2.3072 | 8.2357 | 2.0140 |
| glycerin | 1.8994 | 6.7800 | 1.6580 |
| glyceryl monostearate | 0.3343 | 1.1933 | 0.2918 |
| maltodextrin M180 | 9.9469 | 35.5063 | 8.6829 |
| sucralose | 1.4189 | 5.0647 | 1.2385 |
| Natrosol 250 L | 10.5069 | 37.5053 | 9.1717 |
| Methocel E5 | 0.4932 | 1.7606 | 0.4305 |
| Total mass, mg | 100.0000 | 100.0000 | 24.4544 |
| Theoretical solids, % | 28.0145 | — | — |

TABLE M2

| Component | bulk liquid mg/100 mg | dry film mg/100 mg | dry film mg |
|---|---|---|---|
| water | 59.1217 | — | — |
| acetone | 10.7182 | — | — |

TABLE M2-continued

| Component | bulk liquid mg/100 mg | dry film mg/100 mg | dry film mg |
|---|---|---|---|
| pyridoxine HCl | 2.4449 | 8.1065 | 1.6300 |
| sodium hydroxide | 0.4886 | 1.6201 | 0.3258 |
| sodium metabisulfite | 0.5571 | 1.8471 | 0.3714 |
| disodium EDTA, dihydrate | 0.5589 | 1.8531 | 0.3726 |
| menthol | 2.3341 | 7.7390 | 1.5561 |
| glycerin | 1.6712 | 5.5412 | 1.1142 |
| glyceryl monostearate | 0.3180 | 1.0544 | 0.2120 |
| maltodextrin M180 | 10.0977 | 33.4803 | 6.7320 |
| sucralose | 1.3778 | 4.5684 | 0.9186 |
| Natrosol 250 L | 10.3118 | 34.1900 | 6.8747 |
| Total mass, mg | 100.0000 | 100.0000 | 20.1074 |
| Theoretical solids, % | 30.1601 | — | — |

Neutralizing layer M2 was prepared by combining acetone, glyceryl monostearate, and menthol to form a mixture. The mixture was stirred until a uniform, clear solution was produced. Water was added, and the mixture was stirred. Sodium hydroxide, pyridoxine HCl, sodium metabisulfite, and disodium EDTA dihydrate were then added with stirring until a uniform, clear liquid was produced. Hydroxyethyl cellulose was added to this solution slowly with stirring until a uniform, clear, viscous liquid was produced. Glycerin, maltodextrin, and sucralose were then added with stirring until a uniform, clear, viscous liquid was produced. The resulting mixture was placed under vacuum to eliminate air bubbles. The resulting viscous liquid was cast as a uniform layer onto a separate placebo dried layer (film M1) against an inert support, and dried in an oven. The resulting dried bilayer was removed from the inert support, cut into unit-dose films of a predetermined size (22 mm×22 mm), and subsequently packaged into individual foil pouches. The resulting dried bilayer film was clear/hazy in appearance.

Film N (API Bilayer Film for Trial Studies)

Film N is a bilayer film formed from an apomorphine layer containing components and amounts listed in Table N1 and a neutralizing layer containing the components and amounts listed in Table N2.

The apomorphine layer N1 was prepared by combining acetone, glyceryl monostearate, and menthol with stirring until a uniform, clear solution was produced. Apomorphine hydrochloride (milled to an effective particle size of about 8 µm using a Jet-Pulverizer 2 Micron-Master cyclone discharge mill with stainless steel liner as described in Example 1) was added with stirring, forming an opaque dispersion. Water was added, and the mixture was stirred. Hypromellose was added to this solution slowly with stirring until a uniform, clear liquid was produced. Sodium metabisulfite and disodium EDTA dihydrate were then added with stirring until a uniform liquid was produced. Hydroxyethyl cellulose was added to this solution slowly with stirring until a uniform, clear, viscous liquid was produced. Glycerin, maltodextrin, and sucralose were then added with stirring until a uniform, clear, viscous liquid was produced. The resulting mixture was placed under vacuum to eliminate air bubbles. The viscous liquid was then cast as a uniform layer onto an inert support and dried in an oven. The resulting dried layer was clear/hazy in appearance.

TABLE N1

| Component | bulk liquid mg/100 mg | dry film mg/100 mg | dry film mg |
|---|---|---|---|
| water | 58.6167 | — | — |
| acetone | 10.6170 | — | — |
| sodium metabisulfite | 0.5322 | 1.7297 | 0.4230 |
| disodium EDTA, dihydrate | 0.5325 | 1.7309 | 0.4233 |
| apomorphine HCl | 3.7743 | 12.2677 | 3.0000 |
| menthol | 2.2274 | 7.2397 | 1.7704 |
| glycerin | 1.8489 | 6.0096 | 1.4696 |
| glyceryl monostearate | 0.3171 | 1.0306 | 0.2520 |
| maltodextrin M180 | 9.5753 | 31.1228 | 7.6109 |
| sucralose | 1.3674 | 4.4444 | 1.0869 |
| Natrosol 250 L | 10.1139 | 32.8735 | 8.0390 |
| Methocel E5 | 0.4772 | 1.5511 | 0.3793 |
| Total mass, mg | 100.0000 | 100.0000 | 24.4544 |
| Theoretical solids, % | 30.7662 | — | — |

TABLE N2

| Component | bulk liquid mg/100 mg | dry film mg/100 mg | dry film mg |
|---|---|---|---|
| water | 59.1217 | — | — |
| acetone | 10.7182 | — | — |
| pyridoxine HCl | 2.4449 | 8.1065 | 1.6300 |
| sodium hydroxide | 0.4886 | 1.6201 | 0.3258 |
| sodium metabisulfite | 0.5571 | 1.8471 | 0.3714 |
| disodium EDTA, dihydrate | 0.5589 | 1.8531 | 0.3726 |
| menthol | 2.3341 | 7.7390 | 1.5561 |
| glycerin | 1.6712 | 5.5412 | 1.1142 |
| glyceryl monostearate | 0.3180 | 1.0544 | 0.2120 |
| maltodextrin M180 | 10.0977 | 33.4803 | 6.7320 |
| sucralose | 1.3778 | 4.5684 | 0.9186 |
| Natrosol 250 L | 10.3118 | 34.1900 | 6.8747 |
| Total mass, mg | 100.0000 | 100.0000 | 20.1074 |
| Theoretical solids, % | 30.1601 | — | — |

Neutralizing layer N2 was prepared by combining acetone, glyceryl monostearate, and menthol to form a mixture. The mixture was stirred until a uniform, clear solution was produced. Water was added, and the mixture was stirred. Sodium hydroxide, pyridoxine HCl, sodium metabisulfite, and disodium EDTA dihydrate were then added with stirring until a uniform, clear liquid was produced. Hydroxyethyl cellulose was added to this solution slowly with stirring until a uniform, clear, viscous liquid was produced. Glycerin, maltodextrin, and sucralose were then added with stirring until a uniform, clear, viscous liquid was produced. The resulting mixture was placed under vacuum to eliminate air bubbles. The resulting viscous liquid was cast as a uniform layer onto a separate Apomorphine HCl containing dried layer (film N1) against an inert support, and dried in an oven. The resulting dried bilayer was removed from the inert support, cut into unit-dose films of a predetermined size (22 mm×22 mm), and subsequently packaged into individual foil pouches. The resulting dried bilayer film was clear/hazy in appearance.

When a 3 mg, 22 mm×22 mm unit is placed in 10 mL of pure milliQ water with a stir bar, a pH of between 4.5 and 6.5 is measured.

Example 11—Phase I Trial

A single center phase I trial in 15 healthy subjects was designed to assess the single dose pharmacokinetics, safety and tolerability of a single dose of film N administered in a crossover design. 15 healthy male volunteers are pre-treated with an anti-emetic (10 mg domperidone) for three days. The first day. 12 subjects receive a dose equivalent to 3 mg apomorphine hydrochloride formulated as film N with the drug layer facing down, toward the floor of the mouth. 3 subjects receive the placebo film M. Blood samples (5 ml) are drawn from all subjects prior to dosing, and at 10, 20, 30, 45, 60, 90, 120, 180, 240 minutes post-dose. The blood is immediately centrifuged to recover the plasma which is then stored on dry ice. After a 24 hour washout period, the same subjects are dosed a second time with the same test product and placed in the floor of the mouth but with the drug layer oriented up toward the underside of the tongue.

Assessments include PK determination and local tolerance.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

This application claims benefit of and priority to U.S. Provisional Application No. 61/423,858, filed Dec. 16, 2010, and U.S. Provisional Application No. 61/483,864, filed May 9, 2011, each of which is incorporated by reference herein in its entirety.

Other embodiments are within the claims.

What is claimed is:

1. A pharmaceutical composition in unit dosage form formulated for sublingual administration, wherein said unit dosage form is a film comprising (i) from 2 to 60 mg of an acid addition salt of apomorphine and (ii) from 10±2% to 50±5% (w/w) of a pH neutralizing agent that is an inorganic base selected from the group consisting of inorganic oxides and inorganic hydroxides, wherein said film comprises particles comprising said inorganic base; wherein said unit dosage form further comprises from 3 to 12% (w/w) of plasticizing agent; and wherein said unit dosage form comprises from 30±5% to 65±5% of said acid addition salt of apomorphine.

2. The pharmaceutical composition of claim 1, wherein said unit dosage form comprises from 15±5% to 50±5% (w/w) of said pH neutralizing agent.

3. The pharmaceutical composition of claim 1, wherein said unit dosage form comprises from 10±2% to 25±5% (w/w) of said pH neutralizing agent.

4. The pharmaceutical composition of claim 1, wherein said plasticizing agent is a polyol, oleic acid, or triacetin.

5. The pharmaceutical composition of claim 4, wherein said plasticizing agent is a polyol selected from sorbitol, mannitol, maltitol, xylitol, glycerol, propylene glycol, and polyethylene glycol.

6. The pharmaceutical composition of claim 1, wherein said unit dosage form further comprises from 1 to 50% (w/w) of hydrolyzed starch.

7. The pharmaceutical composition of claim 6, wherein said hydrolyzed starch is a dextrin or a maltodextrin.

8. The pharmaceutical composition of claim 1, wherein said unit dosage form further comprises an antioxidant.

9. The pharmaceutical composition of claim 1, wherein said unit dosage form further comprises from 0.05 to 2.5% (w/w) of metabisulfite.

10. The pharmaceutical composition of claim 1, wherein said unit dosage form further comprises from 0.2 to 5% (w/w) of a permeation enhancer.

11. The pharmaceutical composition of claim 1, wherein said unit dosage form further comprises from 0.2 to 5% (w/w) of glycerol monostearate.

12. The pharmaceutical composition of claim 1, wherein said unit dosage form comprises carboxymethylcellulose, hydroxypropyl cellulose, hydroxypropyl methyl cellulose, hydroxyethyl cellulose, or methyl cellulose.

13. The pharmaceutical composition of claim 1, wherein said unit dosage form comprises 4±1 mg of apomorphine hydrochloride.

14. The pharmaceutical composition of claim 1, wherein said unit dosage form comprises 8±2 mg of apomorphine hydrochloride.

15. The pharmaceutical composition of claim 1, wherein said unit dosage form comprises 10±3 mg of apomorphine hydrochloride.

16. The pharmaceutical composition of claim 1, wherein said unit dosage form comprises 12±3 mg of apomorphine hydrochloride.

17. The pharmaceutical composition of claim 1, wherein the pH neutralizing agent is present in an amount such that a unit dosage form placed in 1 mL of unbuffered water at pH 7 results in a pH of between 2.5 and 8.0.

18. The pharmaceutical composition of claim 1, wherein said acid addition salt of apomorphine is apomorphine hydrochloride.

19. The pharmaceutical composition of claim 1, wherein said unit dosage form is a monolayer film.

20. The pharmaceutical composition of claim 1, wherein said unit dosage form is a bilayer film.

21. The pharmaceutical composition of claim 1, wherein said inorganic base is selected from the group consisting of aluminum hydroxide, calcium hydroxide, magnesium hydroxide, potassium hydroxide, and sodium hydroxide.

22. A method of treating Parkinson's disease in a subject, said method comprising sublingual administration of the pharmaceutical composition of claim 1 in an amount effective to treat said subject.

* * * * *